US006627797B1

(12) United States Patent
Duvick et al.

(10) Patent No.: US 6,627,797 B1
(45) Date of Patent: Sep. 30, 2003

(54) MAIZE LIPOXYGENASE POLYNUCLEOTIDE AND METHODS OF USE

(75) Inventors: Jon Duvick, Des Moines, IA (US); Joyce R. Maddox, Omaha, NE (US); Nancy P. Keller, Madison, WI (US)

(73) Assignees: The Texas A&M University System, College Station, TX (US); Pioneer Hi-Bred International, Inc., Des Moines, IA (US)

(*) Notice: Subject to any disclaimer, the term of this patent is extended or adjusted under 35 U.S.C. 154(b) by 96 days.

(21) Appl. No.: 09/810,268

(22) Filed: Mar. 16, 2001

Related U.S. Application Data
(60) Provisional application No. 60/190,950, filed on Mar. 21, 2000.

(51) Int. Cl.$^7$ .................. C12N 15/09; C12N 15/29; C12N 15/82; A01H 5/00; A01H 5/10
(52) U.S. Cl. .................. 800/279; 800/278; 800/287; 800/298; 800/295; 800/312; 800/314; 800/322; 800/317.1; 800/317.3; 800/306; 435/419; 435/468; 435/320.1; 435/430; 536/23.2; 536/23.6; 536/24.1; 536/24.5
(58) Field of Search ...................... 800/320, 278, 800/279, 298, 295, 312, 314, 322, 317.1, 317.3, 306; 435/419, 468, 320.1, 430; 536/23.2, 23.6, 24.1, 24.5

(56) References Cited

U.S. PATENT DOCUMENTS

| | | |
|---|---|---|
| 5,844,121 A | 12/1998 | Keller |
| 5,942,661 A | 8/1999 | Keller |

OTHER PUBLICATIONS

Hamberg, et al., 1967, *Journal of Bio. Chem.*, 242(22): 5329–5335, "On the Specificity of the Oxygenation of Unsaturated Fatty Acids Catalyzed by Soybean Lipoxidase".
Gardner, et al. 1970, *Lipids*, 5(8): 678–683, "Lipoxygenase From *Zea mays*: 9-$_D$-Hydroperoxy-*trans*-10-, *cis*-12-Octadecadienoic Acid From Linoleic Acid".
Peterman, et al., 1985, *Archives of Biochem. and Biophysics*, 238(2): 476–483, "Immunological Comparison of Lipoxygenase Isozymes-1 and -2 with Soybean Seedling Lipoxygenases".
Funk, et al., 1987, *Biochemistry*, 26: 6880–6884, "Oxygenation of Trans Polyunsaturated Fatty Acids by Lipoxygenase Reveals Steric Features of the Catalytic Mechanism".
Poca, et al., 1990, *Biochem. Biophy. Acta.*, 1045: 107–114, "Lipoxygenases from *Zea mays* L. Purification and physiocochemical characteristics".
Gardner, Harold W., 1991, *Biochem. Biophy. Acta*, 1084: 221–239, "Recent investigations into the lipoxygenase pathway of plants".

Fournier, et al., 1993, *The Plant Journal*, 3(1):63–70, "Purification and characterization of elicitor–induced lipoxygenase in tobacco cells".
Peng, et al., 1994, *Journal of Bio. Chem.*, 269(5): 3755–3761, "A Novel Lipoxygenase from Rice".
Saravitz, et al., 1995, *Plant Physiol.*, 107:535–543, "The Lipoxygenase Isozymes in Soybean [Glycine max (L.) Merr.] Leaves".
Gorlach, et al., 1996, *The Plant Cell*, 8: 629–643, "Benzothiadiazole, a Novel Class of Inducers of Systemic Acquired Resistance, Activates Gene Expression and Disease Resistance in Wheat".
Romero, et al., 1997, *Journ. of Food Science*, 62(4): 696–700, "Rapids Methods for Lipoxygenase Assay in Sweet Corn".
Jensen, et al., 1997, *Plant Mol. Biol.*, 33: 605–614, "Molecular characterization of L2 lipoxygenase from maize embryos".
Prigge, et al., 1997, *Biochimie*, 79: 629–636, "Structure and mechanism of lipoxygenases".
Boyington, et al., 1997, *Adv. Exp. Med. Biol.*, 400A: 133–138, "The Three–Dimensional Structure of Soybean Lipoxygenase–1: An Arachidonic Acid 15–Lipoxygenase".
Hornung, et al., 1999, *Proc. Natl. Acad. Sci.*, 96: 4192–4197, "Conversion of cucmber linoleate 13–lipoxygenase to a 9–lipoxygenating species by site–directed mutagenesis".
Rusterucci, et al., 1999, *Journ. of Bio. Chem.*, 274(51): 36446–36455, "Involvement of Lipoxygenase–dependent Production of Fatty Acid Hydroperoxides in the Development of the Hypersensitive Cell Death induced by Cryptogein on Tobacco Leaves".
Brash, Alan R., 1999, *Journ. of Bio. Chem.*, 274(34): 26379–23682, "Lipoxygenases: Occurrence, Functions, Catalysis, and Acquistion of Substrate".
May, et al., 2000, *Eur. J. Biochem.*, 267: 1100–1109, "The N–terminal β–barrel structure of lipid body lipoxygenase mediates its binding to liposomes and lipid bodies".
Kolomiets, et al., 2000, *Plant Physicol.*, 124: 1121–1130, "A Leaf Lipoxygenase of Potato Induced Specifically by Pathogen Infection".
Wilson, et al., 2001, *MPMI*, 14(8): 980–987, "Cultivar–Dependent Expression of a Maize Lipoxygenase Responsive to Seed Infesting Fungi".

*Primary Examiner*—Elizabeth F. McElwain
*Assistant Examiner*—Medina A. Ibrahim
(74) *Attorney, Agent, or Firm*—Pioneer Hi-Bred International, Inc.

(57) ABSTRACT

The invention provides isolated maize lipoxygenase nucleic acids and their encoded proteins. The present invention provides methods and compositions relating to altering lipoxygenase concentration and/or composition of plants. The invention further provides recombinant expression cassettes, host cells, and transgenic plants.

22 Claims, No Drawings

MAIZE LIPOXYGENASE POLYNUCLEOTIDE AND METHODS OF USE

CROSS REFERENCE TO RELATED APPLICATIONS

This application claims the benefit of U.S. provisional application 60/190,950, filed Mar. 21, 2000, which is herein incorporated by reference.

BACKGROUND OF THE INVENTION

Plant disease outbreaks have resulted in catastrophic crop failures that have triggered famines and caused major social change. Generally, the best strategy for plant disease control is to use resistant cultivars selected or developed by plant breeders for this purpose. However, the potential for serious crop disease epidemics persists today, as evidenced by outbreaks of the Victoria blight of oats and southern corn leaf blight. An additional intractable problem facing farmers worldwide is the contamination of crops by mycotoxins, particularly aflatoxin (AF), a potent carcinogen. During years of high temperatures and drought stress, invasion of kernels by opportunistic seed infesting fungi of the Aspergillus genus, namely *A. parasiticus* and *A. flavus*, is prevalent. These fungi readily produce AFB1, leading to substantial crop loss in developed countries, and significant AF associated health problems in less wealthy countries unable to implement detection and decontamination strategies. Because traditional plant protection and breeding methods are not sufficient to prevent this disease, research efforts have turned to deciphering the molecular events regulating the Aspergillus/seed interaction as a means to develop effective control measures. Accordingly, molecular methods are needed to supplement traditional breeding methods to protect plants from pathogen attack and to reduce levels of mycotoxin.

Lipoxygenase (LOX) is a nonheme iron-containing dioxygenase that catalyzes the regio- and stereo-selective dioxygenation of polyunsaturated fatty acids forming hydroperoxy derivatives. Plant lipoxygenases are classified into 9- and 13-LOXs with respect to their positional specificity of linoleic acid (LA) oxygenation. Widely distributed in the plant and animal kingdom, lipoxygenases play a number of roles. In mammalian cells, lipoxygenases are involved in the biosynthesis of molecules, which mediate inflammatory responses in different tissues. In plants, lipoxygenase expression has been correlated with growth and development, maturation, senescence, wounding and stress, pathogen attack, and biosynthesis of signaling molecules such as jasmonic acid and methyl jasmonate. Increases in host lipoxygenase activity and individual lipoxygenase isozymes after infection with bacterial and fungal pathogens have been observed in a number of plant species.

Oxidation of unsaturated C18 fatty acids by lipoxygenases results in the formation of 9-hydroperoxy 10(E), 12(Z)- and 13-hydroperoxy-9(Z), 11(E)-derivatives of linole(n)ic acids. The hydroperoxy derivatives can serve as substrates for further transformation by 1) the peroxygenase pathway producing epoxides, epoxy alcohols, dihydrodiols/triols; 2) the hydroperoxide lyase pathway producing aldehydes, oxo-acids, and other C6 volatiles; and 3) with the 13-hydroperoxy derivatives, the allene oxide synthase pathway producing cyclized products, alpha- and gamma-ketols.

The present invention describes a maize lipoxygenase, CSSAP92, involved in not only disease resistance to pathogen but also in resistance to aflatoxin contamination. By modulating the level of CSSAP92 in a transgenic plant, it is possible to affect a plant's resistance to disease and/or to reduce the level of aflatoxin contamination in grain.

SUMMARY OF THE INVENTION

Generally, it is the object of the present invention to provide nucleic acids and proteins relating to a maize lipoxygenase, CSSAP92. It is an object of the present invention to provide transgenic plants comprising the nucleic acids of the present invention. It is another object of the present invention to provide methods for modulating, in a transgenic plant, the expression of the nucleic acids of the present invention.

Therefore, in one aspect, the present invention relates to an isolated nucleic acid comprising a member selected from the group consisting of (a) a polynucleotide encoding a polypeptide of the present invention as shown in SEQ ID NO: 3; (b) the polynucleotide having the sequence found in SEQ ID NO: 1 or SEQ ID NO: 2 and (c) a polynucleotide complementary to a polynucleotide of (a) and (b). The isolated nucleic acid can be DNA. The isolated nucleic acid can also be RNA.

In another aspect, the present invention relates to vectors comprising the polynucleotides of the present invention. Also the present invention relates to recombinant expression cassettes, comprising a nucleic acid of the present invention operably linked to a promoter.

In another aspect, the present invention is directed to a host cell into which has been introduced the recombinant expression cassette.

In yet another aspect, the present invention relates to a transgenic plant or plant cell comprising a recombinant expression cassette with a promoter operably linked to any of the isolated nucleic acids of the present invention. Preferred plants containing the recombinant expression cassette of the present invention include but are not limited to maize, soybean, sunflower, sorghum, canola, wheat, alfalfa, cotton, rice barley, and millet. The present invention also provides transgenic seed from the transgenic plant.

In another aspect, the present invention relates to a polypeptide characterized by SEQ ID NO: 3.

In further aspect, the present invention relates to a method of modulating the level of protein in a plant by introducing into a plant cell a recombinant expression cassette comprising a polynucleotide of the present invention operably linked to a promoter; culturing the plant cell under plant growing conditions to produce a regenerated plant; and inducing expression of the polynucleotide for a time sufficient to modulate the protein of the present invention in the plant.

In a further aspect, the present invention relates to a method of decreasing aflatoxin contamination in a plant by introducing into a plant cell a recombinant expression cassette comprising a polynucleotide of the present invention operably linked to a promoter; culturing the plant cell under plant growing conditions to produce a regenerated plant; and inducing expression of the polynucleotide for a time sufficient to reduce aflatoxin contamination in the plant. The polynucleotide may be in the sense or antisense orientation.

In addition, the present invention relates to a method of finding maize lines with reduced levels of CSSAP92 protein comprising the steps of a) generating antibodies to the polypeptide of SEQ ID NO: 3; b) screening maize seeds and identifying seeds with low levels of the polypeptide; c) identifying and cloning the corresponding polynucleotide of the polypeptide; d) identify the allele-specific variations of the cloned polynucleotide; and e) screen maize lines for the allele-specific variations to determine plant lines containing the allele-specific variations.

In another aspect, the present invention relates to a method of increasing 13S-HPODE production in a plant comprising the steps of cloning a polynucleotide which encodes for a N-terminally truncated polypeptide of the present invention operably linked to a promoter, introducing into a plant cell the expression cassette, regenerating a plant from the transformed plant cell, and inducing expression of the fragment for a time sufficient to increase 13S-HPODE production. Preferably the fragment is the 2.6 Kb SalI-NotI fragment of SEQ ID NO: 1.

Further, the present invention relates to methods of increasing resistance in a plant to a pathogen comprising introducing into a plant cell a recombinant expression cassette comprising a polynucleotide of the present invention operably linked to a promoter, regenerating a plant from the transformed plant cell, and inducing expression of the polynucleotide for a time sufficient to increase resistance to a pathogen in the plant. The promoter may be a pathogen-inducible promoter or a tissue-preferred promoter.

Preferred plants and plant cells of the present invention include but are not limited to maize, soybean, sunflower, sorghum, canola, wheat, alfalfa, cotton, rice, barley, and millet. The level of protein in the plant can either be increased or decreased. The polynucleotide can be either in the sense or antisense direction.

BRIEF DESCRIPTION OF THE SEQUENCE DESCRIPTIONS

The following sequence descriptions and sequence listings attached hereto comply with the rules governing nucleotide and/or amino acid sequence disclosures in patent applications as set forth in 37 C. F. R. §1.821–1.825.

SEQ ID NO: 1 is the nucleotide sequence comprising the maize lipoxygenase polynucleotide including the 3' and 5' untranslated regions.

SEQ ID NO: 2 is the nucleotide sequence of the coding region of the maize lipoxygenase polynucleotide.

SEQ ID NO: 3 is the amino acid sequence of the protein encoded by SEQ ID NOS: 1 and 2.

SEQ ID NO: 4 is a designed oligonucleotide based upon the adapter sequence and poly T to remove clones which have a poly A tail but no cDNA.

SEQ ID NO: 5 is the 3' UTR region of CSSAP92 useful for identifying single nucleotide polymorphisms (SNP) that are allele-specific.

DETAILED DESCRIPTION OF THE INVENTION

Overview

The present invention provides, among other things, compositions and methods for modulating (i.e., increasing or decreasing) the level of polynucleotides and polypeptides of the present invention in plants. In particular, the polynucleotides and polypeptides of the present invention can be expressed temporally or spatially, e.g., at developmental stages, in tissues, and/or in quantities, which are uncharacteristic of non-recombinantly engineered plants. Thus, the present invention provides utility in such exemplary applications as manipulating growth and development, maturation, senescence, wounding and stress, pathogen attack, and biosynthesis of signaling molecules such as jasmonic acid and methyl jasmonate.

The present invention also provides isolated nucleic acid comprising polynucleotides of sufficient length and complementarity to a gene of the present invention to use as probes or amplification primers in the detection, quantitation, or isolation of gene transcripts. For example, isolated nucleic acids of the present invention can be used as probes in detecting deficiencies in the level of mRNA in screenings for desired transgenic plants, for detecting mutations in the gene (e.g., substitutions, deletions, or additions), for monitoring upregulation of expression or changes in enzyme activity in screening assays of compounds, for detection of any number of allelic variants (polymorphisms), orthologs, or paralogs of the gene, or for site directed mutagenesis in eukaryotic cells (see, e.g., U.S. Pat. No. 5,565,350). The isolated nucleic acids of the present invention can also be used for recombinant expression of their encoded polypeptides, or for use as immunogens in the preparation and/or screening of antibodies. The isolated nucleic acids of the present invention can also be employed for use in sense, antisense suppression or hairpin dsRNA of one or more genes of the present invention in a host cell, tissue, or plant or by hairpin. Attachment of chemical agents, which bind, intercalate, cleave and/or crosslink to the isolated nucleic acids of the present invention can also be used to modulate transcription or translation. In addition, modification of the native gene to reduce expression can be achieved by chimeric oligonucleotides. The present invention also provides isolated proteins comprising a polypeptide of the present invention (e.g., preproenzyme, proenzyme, or enzymes).

Assays that measure antipathogenic activity are commonly known in the art, as are methods to quantify disease resistance in plants following pathogen infection. See, for example, U.S. Pat. No. 5,614,395, herein incorporated by reference. Such techniques include, measuring over time, the average lesion diameter, the pathogen biomass, and the overall percentage of decayed plant tissues. For example, a plant either expressing an antipathogenic polypeptide or having an antipathogenic composition applied to its surface shows a decrease in tissue necrosis (i.e., lesion diameter) or a decrease in plant death following pathogen challenge when compared to a control plant that was not exposed to the antipathogenic composition. Alternatively, antipathogenic activity can be measured by a decrease in pathogen biomass. For example, a plant expressing an antipathogenic polypeptide or exposed to an antipathogenic composition is challenged with a pathogen of interest. Over time, tissue samples from the pathogen-inoculated tissues are obtained and RNA is extracted. The percent of a specific pathogen RNA transcript relative to the level of a plant specific transcript allows the level of pathogen biomass to be determined. See, for example, Thomma et al. (1998) *Plant Biology* 95:15107–15111, herein incorporated by reference.

Furthermore, in vitro antipathogenic assays include, for example, the addition of varying concentrations of the antipathogenic composition to paper disks and placing the disks on agar containing a suspension of the pathogen of interest. Following incubation, clear inhibition zones develop around the discs that contain an effective concentration of the antipathogenic polypeptide (Liu et al. (1994) *Plant Biology* 91:1888–1892, herein incorporated by reference). Additionally, microspectrophotometrical analysis can be used to measure the in vitro antipathogenic properties of a composition (Hu et al. (1997) *Plant Mol. Biol.* 34:949–959 and Cammue et al. (1992) *J. Biol. Chem.* 267: 2228–2233, both of which are herein incorporated by reference).

The isolated nucleic acids and proteins of the present invention can be used over a broad range of plant types, particularly monocots such as the species of the family Gramineae including Sorghum (e.g. *S. bicolor*), Oryza, Avena, Hordeum, Secale, Triticum and *Zea mays*, and dicots such as Glycine. The isolated nucleic acid and proteins of the present invention can also be used in species from the genera: Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Pisum, Phaseolus, Lolium, and Allium.

Pathogens of the invention include, but are not limited to, viruses or viroids, bacteria, insects, fungi, and the like. Viruses include tobacco or cucumber mosaic virus, ringspot virus, necrosis virus, maize dwarf mosaic virus, etc. Specific fungal and viral pathogens for the major crops include: Soybeans: *Phytophthora megasperma* fsp. *glycinea, Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotichum truncatum*), *Corynespora cassiicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata,* Soybean mosaic virus, *Glomerella glycines,* Tobacco Ring spot virus, Tobacco Streak virus, *Phakopsora pachyrhizi, Pythium aphanidermatum, Pythium ultimum, Pythium debaryanum,* Tomato spotted wilt virus, *Heterodera glycines* Fusarium solani, Canola: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata;* Alfalfa: *Clavibater michiganese* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusar-atrum, Xanthomonas campestris* p.v. *alfalfae, Aphanomyces euteiches, Stemphylium herbarum, Stemphylium alfalfae,* Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondita* f.sp. *tritici, Puccinia striiformis, Pyrenophora triticirepentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana,* Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum,* High Plains Virus, European wheat striate virus; Sunflower: *Plasmophora halstedii, Sclerotinia sclerotiorum,* Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* p.v. *Carotovora, Cephalosporium acremonium, Phytophthora cryptogea, Albugo tragopogonis;* Maize: *Fusarium verticillioides* var. *subglutinans, Erwinia stewartii, Fusarium verticillioides, Gibberella zeae* (*Fusarium graminearum*), *Stenocarpella maydi* (*Diplodia maydis*), *Pythium irregulare, Pythium debaryanum, Pythium graminicola, Pythium splendens, Pythium ultimum, Pythium aphanidermatum, Aspergillus flavus, Bipolaris maydis* O,T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatie-maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganese* subsp. *nebraskense, Trichoderma viride,* Maize Dwarf Mosaic Virus A & B, Wheat Streak Mosaic Virus, Maize Chlorotic Dwarf Virus, *Claviceps sorghi, Pseudonomas avenae, Erwinia chrysanthemi* p.v. *Zea, Erwinia corotovora, Cornstunt spiroplasma, Diplodia macrospora, Sclerophthora macrospora, Peronosclerospora sorghi, Peronosclerospora philippinesis, Peronosclerospora maydis, Peronosclerospora sacchari, Spacelotheca reiliana, Physopella zea, Cephalosporium maydis, Caphalosporium acremonium,* Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola* (*Glomerella graminicola*), *Cercospora sorghi, Gloeocercospora sorghi, Ascochyta sorghina, Pseudomonas syringae* p.v. *syringae, Xanthomonas campestris* p.v. *holcicola Pseudomonas andropogonis, Puccinia purpurea, Macrophomina phaseolina, Perconia circinata, Fusarium verticillioides, Alternaria alternate, Bipolaris sorghicola, Helminthosporium sorghicola, Curvularia lunata, Phoma insidiosa, Pseudomonas avenae* (*Pseudomonas alboprecipitans*), *Ramulispora sorghi, Ramulispora sorghicola, Phyllachara sacchari, Sporisorium reilianum* (*Sphacelotheca reiliana*), *Sphacelotheca cruenta, Sporisorium sorghi,* Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola,* etc.

Definitions

Units, prefixes, and symbols may be denoted in their SI accepted form. Unless otherwise indicated, nucleic acids are written left to right in 5' to 3' orientation, amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology. Principles and Applications,* D H Persing et al., Ed., American Society for Microbiology, Washington, D.C. (1993). The product of amplification is termed an amplicon.

As used herein, "antisense orientation" includes reference to a duplex polynucleotide sequence, which is operably linked to a promoter in an orientation where the antisense strand is transcribed. The antisense strand is sufficiently complementary to an endogenous transcription product such that translation of the endogenous transcription product is often inhibited.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum,* or the ciliate Macronucleus, may be used when the nucleic acid is expressed therein.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. *Nucl. Acids Res.* 17: 477–498 (1989)). Thus, the maize preferred codon for a particular amino acid might be derived from known gene sequences from maize. Maize codon usage for 28 genes from maize plants is listed in Table 4 of Murray et al. , supra.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species, or, if from the same species, is substantially modified from its original form by deliberate human intervention.

By "host cell" is meant a cell, which contains a vector and supports the replication and/or expression of the vector. Host cells may be prokaryotic cells such as *E. Coli,* or eukaryotic cells such as yeast, insect, amphibian, or mammalian cells. Preferably, host cells are monocotyledonous or dicotyledonous plant cells. A particularly preferred monocotyledonous host cell is a maize host cell.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The terms "isolated" refers to material, such as a nucleic acid or a protein, which is: (1) substantially or essentially free from components that normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by non-naturally occurring means to a locus of the genome not native to that nucleic acid. Nucleic acids, which are "isolated", as defined herein, are also referred to as "heterologous" nucleic acids.

As used herein, "marker" includes reference to a locus on a chromosome that serves to identify a unique position on the chromosome. A "polymorphic marker" includes reference to a marker, which appears in multiple forms (alleles) such that different forms of the marker, when they are present in a homologous pair, allow transmission of each of the chromosomes of that pair to be followed. Use of one or a plurality of markers may define a genotype.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules, which comprise and substantially represent the entire transcribed fraction of a genome of a specified organism. Construction of exemplary nucleic acid libraries, such as genomic and cDNA libraries, is taught in standard molecular biology references such as Berger and Kimmel, *Guide to Molecular Cloning Techniques, Methods in Enzymology,* Vol. 152, Academic Press, Inc., San Diego, Calif. (Berger); Sambrook et al., *Molecular Cloning—A Laboratory Manual,* $2^{nd}$ ed., Vol. 1–3 (1989); and *Current Protocols in Molecular Biology,* F. M. Ausubel et al., Eds., Current Protocols, a joint venture between Greene Publishing Associates, Inc. and John Wiley & Sons, Inc. (1994).

As used herein "operably linked" includes reference to a functional linkage between a promoter and a second sequence, wherein the promoter sequence initiates and mediates transcription of the DNA sequence corresponding to the second sequence.

Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds, suspension cultures, embryos, meristematic regions, callus tissue, leaves, roots, shoots, gametophytes, sporophytes, pollen, and microspores. The class of plants, which can be used in the methods of the invention, is generally as broad as the class of higher plants amenable to transformation techniques, including both monocotyledonous and dicotyledonous plants. Preferred plants include, but are not limited to maize, soybean, sunflower, sorghum, canola, wheat, alfalfa, cotton, rice, barley, and millet. A particularly preferred plant is maize (Zea mays).

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide (s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modification have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide", and "protein" are also inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides are not always entirely linear. For instance, polypeptides may be branched as a result of ubiquination, and they may be circular, with or without branching, generally as a result of post-translation events, including natural processing event and events brought about by human manipulation which do not occur naturally. Circular, branched and branched circular polypeptides may be synthesized by non-translation natural process and by entirely synthetic methods, as well.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, underexpressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements, which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The term "selectively hybridizes" includes a reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

The terms "stringent conditions" or "stringent hybridization conditions" include reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides).

Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267–284 (1984): $T_m$=81.5° C.+16.6 (log M)+0.41 (%CG)−0.61 (% form)−500/L; where M is the molarity of monovalent cations, % CG is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$)for the specific sequence and its complement at a defined ionic strength and pH. However, severely stringent conditions can utilize a hybridization and/or wash at 1, 2, 3, or 4° lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel, et al., Eds., Greene Publishing and Wiley-Interscience, New York (1995).

As used herein, "transgenic plant" includes reference to a plant, which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides: (a) "reference sequence", (b) "comparison windows", (c) "sequence identity", and (d) "percentage of sequence identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Optimal alignment of sequences for comparison may be conducted by the local homology algorithm of Smith and Waterman. *Adv. Appl. Math.* 2: 482 (1981); by the homology alignment algorithm of Needleman and Wunsch, *J. Mol. Biol* 48: 443 (1970); by the search for similarity method of Pearson and Lipman, *Proc. Natl. Acad. Sci.* 85: 2444 (1988); by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73: 237–244 (1988); Higgins and Sharp, *CABIOS* 5: 151–153 (1989); Corpet, et al., *Nucleic Acids Research* 16: 10881–90 (1988); Huang, et al, *Computer Applications in the Biosciences* 8: 155–65 (1992), and Pearson, et al., *Methods in Molecular Biology* 24: 307–331 (1994). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995).

GAP uses the algorithm of Needleman and Wunsch (*J. Mol Biol* 48: 443–453 (1970)) to find the alignment of two complete sequences that maximizes the number of matches and minimizes the number of gaps. GAP considers all possible alignments and gap positions and creates the alignment with the largest number of matched bases and the fewest gaps. Default gap creation penalty values and gap extension penalty values in Version 10 of the Wisconsin Genetics Software Package are 8 and 2, respectively, for protein sequences. For nucleotide sequences the default gap creation penalty is 50 while the default gap extension penalty is 3. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50, 60, or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff, *Proc Natl Acad Sci USA* 89:10915). Unless otherwise stated, sequence identity/similarity values provided herein refer to the value obtained using GAP version 10 of Wisconsin Genetic Software Package using default parameters.

(c) As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.,* 4: 11–17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Nucleic Acids

The present invention provides, among other things, isolated nucleic acids of RNA, DNA, and analogs and/or chimeras thereof, comprising a polynucleotide of the present invention.

A polynucleotide of the present invention is inclusive of:
(a) a polynucleotide encoding a polypeptide of SEQ ID NO: 3, including exemplary polynucleotides of SEQ ID NO: 1 and SEQ ID NO: 2;
(b) a polynucleotide which is the product of amplification from a Zea mays nucleic acid library using primer pairs which selectively hybridize under stringent conditions to loci within a polynucleotide selected from the group consisting of SEQ ID NO: 1 and SEQ ID NO: 2;
(c) a polynucleotide which selectively hybridizes to a polynucleotide of (a) or (b);
(d) a polynucleotide having a specified sequence identity with polynucleotides of (a), (b), or (c);
(e) complementary sequences of polynucleotides of (a), (b), (c), r (d);
(f) a polynucleotide comprising at least a specific number of contiguous nucleotides from a polynucleotide of (a), (b), (c), (d), or (e); and
(g) an isolated polynucleotide made by the process of: 1) providing a full-length enriched nucleic acid library, 2) selectively hybridizing the polynucleotide to a polynucleotide of (a), (b), (c), (d), (e), (f), (g), or (h), thereby isolating the polynucleotide from the nucleic acid library.

The present invention provides, among other things, isolated nucleic acids of RNA, DNA, and analogs and/or chimeras thereof, comprising a polynucleotide of the present invention.

A. Polynucleotides Encoding A Polypeptide of the Present Invention

The present invention provides isolated nucleic acids comprising a polynucleotide of the present invention, wherein the polynucleotide encodes a polypeptide of the present invention. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Thus, each silent variation of a nucleic acid, which encodes a polypeptide of the present invention, is implicit in each described polypeptide sequence and is within the scope of the present invention. Accordingly, the present invention includes polynucleotides of the present invention and polynucleotides encoding a polypeptide of the present invention.

B. Polynucleotides Amplified from a Plant Nucleic Acid Library

The present invention provides an isolated nucleic acid comprising a polynucleotide of the present invention, wherein the polynucleotides are amplified, under nucleic acid amplification conditions, from a plant nucleic acid library. Nucleic acid amplification conditions for each of the variety of amplification methods are well known to those of ordinary skill in the art. The plant nucleic acid library can be constructed from a monocot such as a cereal crop. Exemplary cereals include corn, sorghum, alfalfa, canola, wheat, or rice. The plant nucleic acid library can also be constructed from a dicot such as soybean. *Zea mays* lines B73, PHRE1, A632, BMS-P2#10, W23, and Mol 7 are known and publicly available. Other publicly known and available maize lines can be obtained from the Maize Genetics Cooperation (Urbana, Ill.). Wheat lines are available from the Wheat Genetics Resource Center (Manhattan, Kans.).

The nucleic acid library may be a cDNA library, a genomic library, or a library generally constructed from nuclear transcripts at any stage of intron processing. cDNA libraries can be normalized to increase the representation of relatively rare cDNAs. In optional embodiments, the cDNA library is constructed using an enriched full-length cDNA synthesis method. Examples of such methods include Oligo-Capping (Maruyama, K. and Sugano, S. *Gene* 138: 171–174, 1994), Biotinylated CAP Trapper (Carninci, et al. *Genomics* 37: 327–336, 1996), and CAP Retention Procedure (Edery, E., Chu, L. L., et al. *Molecular and Cellular Biology* 15: 3363–3371, 1995). Rapidly growing tissues or rapidly dividing cells are preferred for use as an mRNA source for construction of a cDNA library. Growth stages of corn is described in "How a Corn Plant Develops," Special Report No. 48, Iowa State University of Science and Technology Cooperative Extension Service, Ames, Iowa, Reprinted February 1993.

A polynucleotide of this embodiment (or subsequences thereof) can be obtained, for example, by using amplification primers which are selectively hybridized and primer extended, under nucleic acid amplification conditions, to at least two sites within a polynucleotide of the present invention, or to two sites within the nucleic acid which flank and comprise a polynucleotide of the present invention, or to a site within a polynucleotide of the present invention and a site within the nucleic acid which comprises it. Methods for obtaining 5' and/or 3' ends of a vector insert are well known in the art. See, e.g., RACE (Rapid Amplification of Complementary Ends) as described in Frohman, M. A., in PCR Protocols: A Guide to Methods and Applications, M. A. Innis, D. H. Gelfand, J. J. Sninsky, T. J. White, Eds. (Academic Press, Inc., San Diego), pp. 28–38 (1990)); see also, U.S. Pat. No. 5,470,722, and *Current Protocols in Molecular* Biology, Unit 15.6, Ausubel, et al., Eds., Greene Publishing and Wiley-Interscience, New York (1995); Frohman and Martin, *Techniques* 1:165 (1989).

Optionally, the primers are complementary to a subsequence of the target nucleic acid which they amplify but may have a sequence identity ranging from about 85% to 99% relative to the polynucleotide sequence which they are designed to anneal to. As those skilled in the art will appreciate, the sites to which the primer pairs will selectively hybridize are chosen such that a single contiguous nucleic acid can be formed under the desired nucleic acid amplification conditions. The primer length in nucleotides is selected from the group of integers consisting of from at least 15 to 50. Thus, the primers can be at least 15, 18, 20, 25, 30, 40, or 50 nucleotides in length. Those of skill will recognize that a lengthened primer sequence can be employed to increase specificity of binding (i.e., annealing) to a target sequence. A non-annealing sequence at the 5' end of a primer (a "tail") can be added, for example, to introduce a cloning site at the terminal ends of the amplicon.

The amplification products can be translated using expression systems well known to those of skill in the art. The resulting translation products can be confirmed as polypeptides of the present invention by, for example, assaying for the appropriate catalytic activity (e.g., specific activity and/or substrate specificity), or verifying the presence of one or more linear epitopes, which are specific to a polypeptide of the present invention. Methods for protein synthesis from PCR derived templates are known in the art and available commercially. See, e.g., Amersham Life Sciences, Inc, Catalog '97, p.354.

C. Polynucleotides Which Selectively Hybridize to a Polynucleotide of (A) or (B)

The present invention provides isolated nucleic acids comprising polynucleotides of the present invention, wherein the polynucleotides selectively hybridize, under selective hybridization conditions, to a polynucleotide of section (A) or (B) as discussed above. Thus, the polynucleotides of this embodiment can be used for isolating, detecting, and/or quantifying nucleic acids comprising the polynucleotides of (A) or (B). For example, polynucleotides of the present invention can be used to identify, isolate, or amplify partial or full-length clones in a deposited library. In some embodiments, the polynucleotides are genomic or cDNA sequences isolated or otherwise complementary to a cDNA from a dicot or monocot nucleic acid library. Exemplary species of monocots and dicots include, but are not limited to: maize, canola, soybean, cotton, wheat, sorghum, sunflower, alfalfa, oats, sugar cane, millet, barley, and rice. The cDNA library comprises at least 50% to 95% full-length sequences (for example, at least 50%, 60%, 70%, 80%, 90%, or 95% full-length sequences). The cDNA libraries can be normalized to increase the representation of rare sequences. See, e.g., U.S. Pat. No. 5,482,845. Low stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% to 80% sequence identity and can be employed to identify orthologous or paralogous sequences.

D. Polynucleotides Having a Specific Sequence Identity with the Polynucleotides of (A), (B) or (C)

The present invention provides isolated nucleic acids comprising polynucleotides of the present invention, wherein the polynucleotides have a specified identity at the nucleotide level to a polynucleotide as disclosed above in sections (A), (B), or (C), above. Identity can be calculated using, for example, the BLAST or GAP algorithms under default conditions. The percentage of identity to a reference sequence is at least 60% and, rounded upwards to the nearest integer, can be expressed as an integer selected from the group of integers consisting of from 60 to 99. Thus, for example, the percentage of identity to a reference sequence can be at least 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

E. Polynucleotides Encoding a Protein Having a Subsequence from a Prototype Polypeptide and Cross-Reactive to the Prototype Polypeptide The present invention provides isolated nucleic acids comprising polynucleotides of the present invention, wherein the polynucleotides encode a protein having a subsequence of contiguous amino acids from a prototype polypeptide of the present invention such as are provided in (A), above. The length of contiguous amino acids from the prototype polypeptide is selected from the group of integers consisting of from at least 10 to the number of amino acids within the prototype sequence. Thus, for example, the polynucleotide can encode a polypeptide having a subsequence having at least 10, 15, 20, 25, 30, 35, 40, 45, or 50, contiguous amino acids from the prototype polypeptide. Further, the number of such subsequences encoded by a polynucleotide of the instant embodiment can be any integer selected from the group consisting of from 1 to 20, such as 2, 3, 4, or 5. The subsequences can be separated by any integer of nucleotides from 1 to the number of nucleotides in the sequence such as at least 5, 10, 15, 25, 50, 100, or 200 nucleotides.

The proteins encoded by polynucleotides of this embodiment, when presented as an immunogen, elicit the production of polyclonal antibodies which specifically bind to a prototype polypeptide such as but not limited to, a polypeptide encoded by the polynucleotide of (A) or (B), above. Generally, however, a protein encoded by a polynucleotide of this embodiment does not bind to antisera raised against the prototype polypeptide when the antisera has been fully immunosorbed with the prototype polypeptide. Methods of making and assaying for antibody binding specificity/affinity are well known in the art Exemplary immunoassay formats include ELISA, competitive immunoassays, radioimmunoassays, Western blots, indirect immunofluorescent assays and the like.

In a preferred assay method, fully immunosorbed and pooled antisera, which is elicited to the prototype polypeptide, can be used in a competitive binding assay to test the protein. The concentration of the prototype polypeptide required to inhibit 50% of the binding of the antisera to the prototype polypeptide is determined. If the amount of the protein required to inhibit binding is less than twice the amount of the prototype protein, then the protein is said to specifically bind to the antisera elicited to the immunogen. Accordingly, the proteins of the present invention embrace allelic variants, conservatively modified variants, and minor recombinant modifications to a prototype polypeptide.

A polynucleotide of the present invention optionally encodes a protein having a molecular weight as the non-glycosylated protein within 20% of the molecular weight of the full-length non-glycosylated polypeptides of the present invention. Molecular weight can be readily determined by SDS-PAGE under reducing conditions. Optionally, the molecular weight is within 15% of a full length polypeptide of the present invention, more preferably within 10% or 5%, and most preferably within 3%, 2%, or 1% of a full length polypeptide of the present invention.

Optionally, the polynucleotides of this embodiment will encode a protein having a specific enzymatic activity at least 50%, 60%, 80%, or 90% of a cellular extract comprising the native, endogenous full-length polypeptide of the present invention. Further, the proteins encoded by polynucleotides of this embodiment will optionally have a substantially similar affinity constant ($K_m$) and/or catalytic activity (i.e., the microscopic rate constant, $k_{cat}$) as the native endogenous, full-length protein. Those of skill in the art will recognize that $k_{cat}/K_m$ value determines the specificity for competing substrates and is often referred to as the specificity constant. Proteins of this embodiment can have a $k_{cat}/K_m$ value at least 10% of a full-length polypeptide of the present invention as determined using the endogenous substrate of that polypeptide. Optionally, the $k_{cat}/K_m$ value will be at least 20%, 30%, 40%, 50%, and most preferably at least 60%, 70%, 80%, 90%, or 95% the $k_{cat}/K_m$ value of the full-length polypeptide of the present invention. Determination of $k_{cat}$, $K_m$, and $k_{cat}/K_m$ can be determined by any number of means well known to those of skill in the art. For example, the initial rates (i.e., the first 5% or less of the reaction) can be determined using rapid mixing and sampling techniques (e.g., continuous-flow, stopped-flow, or rapid quenching techniques), flash photolysis, or relaxation methods (e.g., temperature jumps) in conjunction with such exemplary methods of measuring as spectrophotometry, spectrofluorimetry, nuclear magnetic resonance, or radioactive procedures. Kinetic values are conveniently obtained using a Lineweaver-Burk or Eadie-Hofstee plot.

F. Polynucleotides Complementary to the Polynucleotides of (A)–(E)

The present invention provides isolated nucleic acids comprising polynucleotides complementary to the polynucleotides of sections A–E, above. As those of skill in the art will recognize, complementary sequences base pair throughout the entirety of their length with the polynucleotides of sections (A)–(E) (i.e., have 100% sequence identity over their entire length). Complementary bases associate through hydrogen bonding in double stranded nucleic acids. For example, the following base pairs are complementary: guanine and cytosine; adenine and thymine; and adenine and uracil.

G. Polynucleotides That are Subsequences of the Polynucleotides of the Present Invention The present invention provides isolated nucleic acids comprising polynucleotides which comprise at least 15 contiguous bases from the polynucleotides of the present invention as discussed above. The length of the polynucleotide is given as an integer selected from the group consisting of from at least 15 to the length of the nucleic acid sequence from which the polynucleotide is a subsequence of. Thus, for example, polynucleotides of the present invention are inclusive of polynucleotides comprising at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 85, 90, 95, 100, 110, 120, 130, 140, 150, 160, 170, 180, 190, 200, 210, 220, 230, 240, 250, 260, 270, 280, 290, 300, 350, 400, 450, 500, 550, 600, 650, 700, 750, 800, 850, 900, 950, or 1000 contiguous nucleotides in length from the polynucleotides of (A)–(F). Optionally, the number of such subsequences encoded by a polynucleotide of the instant embodiment can be any integer selected from the group consisting of from 1 to 1000, such as 2, 3, 4, or 5. The subsequences can be separated by any integer of nucleotides from 1 to the number of nucleotides in the sequence such as at least 5, 10, 15, 20, 25, 30, 35, 40, 45, 50, 75, 100, 200, 300, 400, 500, 600, 700, 800, 900, or 1000 nucleotides.

Subsequences can be made by in vitro synthetic, in vitro biosynthetic, or in vivo recombinant methods. In optional embodiments, subsequences can be made by nucleic acid amplification. For example, nucleic acid primers will be constructed to selectively hybridize to a sequence (or its complement) within, or co-extensive with, the coding region.

The subsequences of the present invention can comprise structural characteristics of the sequence from which it is derived. Alternatively, the subsequences can lack certain structural characteristics of the larger sequence from which it is derived such as a poly (A) tail. Optionally, a subsequence from a polynucleotide encoding a polypeptide having at least one linear epitope in common with a prototype polypeptide sequence as provided in (a), above, may encode an epitope in common with the prototype sequence.

Alternatively, the subsequence may not encode an epitope in common with the prototype sequence but can be used to isolate the larger sequence by, for example, nucleic acid hybridization with the sequence from which it's derived. Subsequences can be used to modulate or detect gene expression by introducing into the subsequences compounds which bind, intercalate, cleave and/or crosslink to nucleic acids. Exemplary compounds include acridine, psoralen, phenanthroline, naphthoquinone, daunomycin or chloroethylaminoaryl conjugates.

H. Polynucleotides From a Full-length Enriched cDNA Library Having the Physico-Chemical Property of Selectively Hybridizing to a Polynucleotide of (A)–(G)

The present invention provides an isolated polynucleotide from a full-length enriched cDNA library having the physico-chemical property of selectively hybridizing to a polynucleotide of paragraphs (A), (B), (C), (D), (E), (F), or (G) as discussed above. Methods of constructing full-length enriched cDNA libraries are known in the art and discussed briefly below. The cDNA library comprises at least 50% to 95% full-length sequences (for example, at least 50%, 60%, 70%, 80%, 90%, or 95% full-length sequences). The cDNA library can be constructed from a variety of tissues from a monocot or dicot at a variety of developmental stages. Exemplary species include maize, wheat, rice, canola, soybean, cotton, sorghum, sunflower, alfalfa, oats, sugar cane, millet, barley, and rice. Methods of selectively hybridizing, under selective hybridization conditions, a polynucleotide from a full-length enriched library to a polynucleotide of the present invention are known to those of ordinary skill in the art. Any number of stringency conditions can be employed to allow for selective hybridization. In optional embodiments, the stringency allows for selective hybridization of sequences having at least 70%, 75%, 80%, 85%, 90%, 95%, or 98% sequence identity over the length of the hybridized region. Full-length enriched cDNA libraries can be normalized to increase the representation of rare sequences.

I. Polynucleotide Products Made by an cDNA Isolation Process

The present invention provides an isolated polynucleotide made by the process of: 1) providing a full-length enriched nucleic acid library, 2) selectively hybridizing the polynucleotide to a polynucleotide of paragraphs (A), (B), (C), (D), (E), (F), (G), or (H) as discussed above, and thereby isolating the polynucleotide from the nucleic acid library. Full-length enriched nucleic acid libraries are constructed as discussed in paragraph (G) and below. Selective hybridization conditions are as discussed in paragraph (G). Nucleic acid purification procedures are well known in the art. Purification can be conveniently accomplished using solid-phase methods; such methods are well known to those of skill in the art and kits are available from commercial suppliers such as Advanced Biotechnologies (Surrey, UK). For example, a polynucleotide of paragraphs (A)–(H) can be immobilized to a solid support such as a membrane, bead, or particle. See, e.g., U.S. Pat. No. 5,667,976. The polynucleotide product of the present process is selectively hybridized to an immobilized polynucleotide and the solid support is subsequently isolated from non-hybridized polynucleotides by methods including, but not limited to, centrifugation, magnetic separation, filtration, electrophoresis, and the like.

Construction of Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a monocot.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. A polynucleotide of the present invention can be attached to a vector, adapter, or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid of the present invention less the length of its polynucleotide of the present invention is less than 20 kilobase pairs, often less than 15 kb, and frequently less than 10 kb. Use of cloning vectors, expression vectors, adapters, and linkers is well known and extensively described in the art. For a description of various nucleic acids see, for example, Stratagene Cloning Systems, Catalogs 1999 (La Jolla, Calif.); and, Amersham Life Sciences, Inc, Catalog '99 (Arlington Heights, Ill.).

A. Recombinant Methods for Constructing Nucleic Acids

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes, which selectively hybridize, under stringent conditions, to the polynucleotides of the present invention are used to identify the desired sequence in a cDNA or genomic DNA library. Isolation of RNA and construction of cDNA and genomic libraries is well known to those of ordinary skill in the art. See, e.g., *Plant Molecular Biology: A Laboratory Manual*, Clark, Ed., Springer-Verlag, Berlin (1997); and, *Current Protocols in Molecular Biology*, Ausubel, et al., Eds., Greene Publishing and Wiley-Interscience, New York (1995).

A1. Full-length Enriched cDNA Libraries

A number of cDNA synthesis protocols have been described which provide enriched full-length cDNA libraries. Enriched full-length cDNA libraries are constructed to comprise at least 60%, and more preferably at least 70%, 80%, 90% or 95% full-length inserts amongst clones containing inserts. The length of insert in such libraries can be at least 2,3, 4, 5, 6, 7, 8, 9, 10 or more kilobase pairs. Vectors to accommodate inserts of these sizes are known in the art and available commercially. See, e.g., Stratagene's lambda ZAP Express (cDNA cloning vector with 0 to 12 kb cloning capacity). An exemplary method of constructing a greater than 95% pure full-length cDNA library is described by Carninci et al., *Genomics*, 37:327–336 (1996). Other methods for producing full-length libraries are known in the art. See, e.g., Edery et al., *Mol. Cell Biol.*, 15(6):3363–3371 (1995); and, PCT Application WO 96/34981.

A2 Normalized or Subtracted cDNA Libraries

A non-normalized cDNA library represents the mRNA population of the tissue it was made from. Since unique clones are out-numbered by clones derived from highly expressed genes their isolation can be laborious. Normalization of a cDNA library is the process of creating a library in which each clone is more equally represented. Construction of normalized libraries is described in Ko, *Nucl. Acids. Res.*, 18(19):5705–5711 (1990); Patanjali et al., Proc. Natl. Acad USA., 88:1943–1947 (1991); U.S. Pat. Nos. 5,482,685, 5,482,845, and 5,637,685. In an exemplary method described by Soares et al., normalization resulted in reduction of the abundance of clones from a range of four orders of magnitude to a narrow range of only 1 order of magnitude. *Proc. Natl. Acad. Sci. USA,* 91:9228–9232 (1994).

Subtracted cDNA libraries are another means to increase the proportion of less abundant cDNA species. In this procedure, cDNA prepared from one pool of mRNA is depleted of sequences present in a second pool of mRNA by hybridization. The cDNA:mRNA hybrids are removed and the remaining un-hybridized cDNA pool is enriched for sequences unique to that pool. See, Foote et al. in, *Plant Molecular Biology: A Laboratory Manual,* Clark, Ed., Springer-Verlag, Berlin (997); Kho and Zarbi, *Technique,* 3(2):58–63 (1991); Sive and St. John, *Nucl. Acids Res.,* 16(22):10937 (1988); *Current Protocols in Molecular Biology,* Ausubel, et al., Eds., Greene Publishing and Wiley-Interscience, New York (1995); and, Swaroop et al., *Nucl. Acids Res.,* 19(17):4725–4730 (1991). cDNA subtraction kits are commercially available. See, e.g., PCR-Select (Clontech, Palo Alto, Calif.).

To construct genomic libraries, large segments of genomic DNA are generated by fragmentation, e.g. using restriction endonucleases, and are ligated with vector DNA to form concatemers that can be packaged into the appropriate vector. Methodologies to accomplish these ends, and sequencing methods to verify the sequence of nucleic acids are well known in the art. Examples of appropriate molecular biological techniques and instructions sufficient to direct persons of skill through many construction, cloning, and screening methodologies are found in Sambrook, et al., *Molecular Cloning. A Laboratory Manual,* 2nd Ed., Cold Spring Harbor Laboratory Vols. 1–3 (1989), Methods in Enzymology, Vol. 152: *Guide to Molecular Cloning Techniques,* Berger and Kimmel, Eds., San Diego: Academic Press, Inc. (1987), *Current Protocols in Molecular Biology,* Ausubel, et al., Eds., Greene Publishing and Wiley-Interscience, New York (1995); *Plant Molecular Biology. A Laboratory Manual,* Clark, Ed., Springer-Verlag, Berlin (1997). Kits for construction of genomic libraries are also commercially available.

The cDNA or genomic library can be screened using a probe based upon the sequence of a polynucleotide of the present invention such as those disclosed herein. Probes may be used to hybridize with genomic DNA or cDNA sequences to isolate homologous genes in the same or different plant species. Those of skill in the art will appreciate that various degrees of stringency of hybridization can be employed in the assay; and either the hybridization or the wash medium can be stringent.

The nucleic acids of interest can also be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. The T4 gene 32 protein (Boehringer Mannheim) can be used to improve yield of long PCR products.

PCR-based screening methods have been described. Wilfinger et al. describe a PCR-based method in which the longest cDNA is identified in the first step so that incomplete clones can be eliminated from study. *Bio Techniques,* 22(3): 481–486 (1997). Such methods are particularly effective in combination with a full-length cDNA construction methodology, above.

B. Synthetic Methods for Constructing Nucleic Acids

The isolated nucleic acids of the present invention can also be prepared by direct chemical synthesis by methods such as the phosphotriester method of Narang et al., *Meth. Enzymol.* 68: 90–99 (1979); the phosphodiester method of Brown et al., *Meth. Enzymol.* 68: 109–151 (1979); the diethylphosphoramidite method of Beaucage et al., *Tetra. Lett.* 22: 1859–1862 (1981); the solid phase phosphoramidite triester method described by Beaucage and Caruthers, *Tetra. Letts.* 22(20): 1859–1862 (1981), e.g., using an automated synthesizer, e.g., as described in Needham-VanDevanter et al., *Nucleic Acids Res.,* 12: 6159–6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is best employed for sequences of about 100 bases or less, longer sequences may be obtained by the ligation of shorter sequences.

Recombinant Expression Cassettes

The present invention further provides recombinant expression cassettes comprising a nucleic acid of the present invention. A nucleic acid sequence coding for the desired polynucleotide of the present invention, for example a cDNA or a genomic sequence encoding a full length polypeptide of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plan expression vectors may also contain, if desired, a promoter regulatory region (e.g., one conferring inducible or constitutive, environmentally- or developmentally-regulated, or cell- or tissue-specific/ selective expression), a transcription initiation start site, a ribosome binding site, an RNA processing signal, a transcription termination site, and/or a polyadenylation signal.

A number of promoters can be used in the practice of the invention. A plant promoter fragment can be employed which will direct expression of a polynucleotide of the present invention in all tissues of a regenerated plant. Such promoters are referred to herein as "constitutive" promoters and are active under most environmental conditions and state of development or cell differentiation. Examples of constitutive promoters include the cauliflower mosaic virus (CaMV) 35S transcription initiation region, the 1'- or 2'-promoter derived from T-DNA of *Agrobacterium tumefaciens,* the ubiquitin 1 promoter (Christensen, et al. *Plant Mol Biol* 18, 675–689 (1992); Bruce, et al., *Proc Natl Acad Sci USA* 86, 9692–9696 (1989)), the Smas promoter, the cinnamyl alcohol dehydrogenase promoter (U.S. Pat. No, 5,683,439), the Nos promoter, the pEmu promoter, the rubisco promoter, the GRP 1–8 promoter, the maize constitutive promoters described in PCT Publication No. WO 99/43797 which include the histone H2B, metallothionein, alpha-tubulin 3, elongation factor efla, ribosomal protein rps8, chlorophyll a/b binding protein, and glyceraldehyde-3-phosphate dehydrogenase promoters, and other transcription initiation regions from various plant genes known to those of skill. A preferred promoter of the present invention is ubiquitin. In addition, a preferred promoter of the present invention is a pathogen-inducible promoter, such as the PRms promoter.

Where low level expression is desired, weak promoters will be used. It is recognized that weak inducible promoters may be used. Additionally, either a weak constitutive or a weak tissue specific promoter may be used. Generally, by a "weak promoter" is intended a promoter that drives expression of a coding sequence at a low level. By low level is intended at levels of about 1/1000 transcripts to about 1/100,000 transcripts to about 1/500,000 transcripts. Alternatively, it is recognized that weak promoters also encompass promoters that are expresses in only a few cells and not in others to give a total low level of expression. Such weak constitutive promoters include, for example, the core promoter of the Rsyn7 (PCT Publication No. WO 97/44756), the core 35S CaMV promoter, and the like. Where a promoter is expressed at unacceptably high levels, portions of the promoter sequence can be deleted or modified to decrease expression levels. Additionally, to obtain a varied series in the level of expression, one can also make a set of transgenic plants containing the polynucleotides of the present invention with a strong constitutive promoter, and then rank the transgenic plants according to the observed level of expression. The transgenic plants will show a variety in performance, from high expression to low expression. Factors such as chromosomal position effect, cosuppression, and the like will affect the expression of the polynucleotide.

Alternatively, the plant promoter can direct expression of a polynucleotide of the present invention under environmental control. Such promoters are referred to here as "inducible" promoters. Environmental conditions that may effect transcription by inducible promoters include pathogen attack, anaerobic conditions, or the presence of light. Examples of inducible promoters are the Adh1 promoter, which is inducible by hypoxia or cold stress, the Hsp70 promoter, which is inducible by heat stress, and the PPDK promoter, which is inducible by light. Examples of pathogen-inducible promoters include those from proteins, which are induced following infection by a pathogen; e.g., PR proteins, SAR proteins, beta-1,3-glucanase, chitinase, etc. See, for example, Redolfi, et al., *Meth J. Plant Pathol.* 89:245–254 (1983); Uknes et al., *The Plant Cell* 4:645–656 (1992); Van Loon, *Plant Mol. Virol.* 4:111–116 (1985); PCT Publication No. WO 99/43819.

Of interest are promoters that are expressed locally at or near the site of pathogen infection. See, for example, Marineau, et al., *Plant Mol Biol* 9:335–342 (1987); Matton, et al., *Molecular Plant-Microbe Interactions* 2:325–342 (1987); Somssich et al., *Proc Natl Acad Sci USA* 83:2427–2430 (1986); Somssich et al., *Mole Gen Genetics* 2:93–98 (1988); Yang, *Proc Natl Acad Sci USA* 93:14972–14977. See also, Chen, et al., *Plant J* 10:955–966 (1996); Zhang and Sing, *Proc Natl Acad Sci USA* 91:2507–2511 (1994); Warner, et al., *Plant J* 3:191–201 (1993), and Siebertz, et al., *Plant Cell* 1:961–968 (1989), all of which are herein incorporated by reference. Of particular interest is the inducible promoter for the maize PRms gene, whose expression is induced by the pathogen *Fusarium verticillioides* (see, for example, Cordero, et al., *Physiol Molec Plant Path* 41: 189–200 (1992) and is herein incorporated by reference.

Additionally, as pathogens find entry into plants through wounds or insect damage, a wound inducible promoter may be used in the constructs of the invention. Such wound inducible promoters include potato proteinase inhibitor (pin II) gene (Ryan, *Annu Rev Phytopath* 28:425–449 (1990); Duan, et al., *Nat Biotech* 14:494–498 (1996)); wun1 and wun 2, U.S. Pat. No. 5,428,148; win1 and win2 (Stanford et al., *Mol Gen Genet* 215:200–208 (1989)); systemin (McGurt, et al., *Science* 225:1570–1573 (1992)); WIP1 (Rohmeier, et al., *Plant Mol Biol* 22:783–792 (1993); Eckelkamp, et al., *FEB Letters* 323:73–76 (1993)); MPI gene (Cordero, et al., *The Plant J* 6(2):141–150(1994)); and the like, herein incorporated by reference.

Examples of promoters under developmental control include promoters that initiate transcription only, or preferentially, in certain tissues, such as leaves, roots, fruit, seeds, or flowers. These promoters are sometimes called tissue-preferred promoters. Exemplary promoters include the anther specific promoter 5126 (U.S. Pat. Nos. 5,689,049 and 5,689,051), glob-1 promoter, and gamma-zein promoter. An exemplary promoter for leaf- and stalk-preferred expression is MS8–15 (PCT Publication no. WO 98/00533). Examples of seed-preferred promoters included, but are not limited to, 27 kD gamma zein promoter and waxy promoter (Boronat, et al., *Plant Sci,* 47:95–102 (1986); Reina, et al, *Nucleic Acids Res* 18(21):6426 (1990); and Kloesgen, et al, *Mol Gen Genet* 203:237–244 (1986)). Promoters that express in the embryo, pericarp, and endosperm are disclosed in PCT Publication no. WO 00/11177 and WO 00/12733 both of which are hereby incorporated by reference. The operation of a promoter may also vary depending on its location in the genome. Thus, a developmentally regulated promoter may become fully or partially constitutive in certain locations. A developmentally regulated promoter can also be modified, if necessary, for weak expression.

Both heterologous and non-heterologous (i.e. endogenous) promoters can be employed to direct expression of the nucleic acids of the present invention. These promoters can also be used, for example, in recombinant expression cassettes to drive expression of antisense nucleic acids to reduce, increase, or alter concentration and/or composition of the proteins of the present invention in a desired tissue. Thus, in some embodiments, the nucleic acid construct will comprise a promoter functional in a plant cell, such as in *Zea Mays,* operably linked to a polynucleotide of the present invention. Promoters useful in these embodiments include the endogenous promoters driving expression of a polypeptide of the present invention.

In some embodiments, isolated nucleic acids which serve as promoter or enhancer elements can be introduced in the appropriate position (generally upstream) of a non-heterologous form of a polynucleotide of the present invention so as to up or down regulate expression of a polynucleotide of the present invention. For example, endogenous promoters can be altered in vivo by mutation, deletion, and/or substitution (see, Kmiec, U.S. Pat. No. 5,565,350; Zarling et al., PCT/US93/03868), or isolated promoters can be introduced into a plant cell in the proper orientation and distance from a gene of the present invention so as to control the expression of the gene. Gene expression can be modulated under conditions suitable for plant growth so as to alter the total concentration and/or alter the composition of the polypeptides of the present invention in plant cell. Thus, the present invention provides compositions, and methods for making, heterologous promoters and/or enhancers operably linked to a native, endogenous (i.e., non-heterologous) form of a polynucleotide of the present invention.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold, Buchman and Berg, *Mol. Cell biol.* 8: 4395–4405 (1988); Callis et al., *Genes Dev.* 1: 1183–1200 (1987). Such intron enhancement of gene expression is typically greatest when placed near the 5' end of the transcription unit. Use of the maize introns Adh1-S intron 1, 2, and 6, the Bronze-1 intron are known in the art. See generally, *The Maize Handbook*, Chapter 116, Freeling and Walbot, Eds., Springer, New York (1994).

The vector comprising the sequences from a polynucleotide of the present invention will typically comprise a marker gene, which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase NPTII) gene encoding kanamycin or geneticin resistance, the hygromycin phosphotransferase (NPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS gene encodes resistance to the herbicide chlorsulfuron.

Typical vectors useful for expression of genes in higher plants are well known in the art and include vectors derived from the tumor-induced (Ti) plasmid of *Agrobacterium tumefaciens* described by Rogers et al., Meth. In Enzymol., 153:253–277 (1987). These vectors are plant integrating vectors in that upon transformation, the vectors integrate a portion of vector DNA into the genome of the host plant. Exemplary *A. tumefaciens* vectors useful herein are plasmids pKYLX6 and pKYLX7 of Schardl et al., Gene, 61:1–11(1987) and Berger et al., Proc. Natl. Acad. Sci. U.S.A., 86:8402–8406 (1989). Another useful vector herein is plasmid pBI101.2 that is available from Clontech Laboratories, Inc. (Palo Alto, Calif.).

A polynucleotide of the present invention can be expressed in either sense or anti-sense orientation as desired.

It will be appreciated that control of gene expression in either sense or anti-sense orientation can have a direct impact on the observable plant characteristics. Antisense technology can be conveniently used to inhibit gene expression in plants. To accomplish this, a nucleic acid segment from the desired gene is cloned and operably linked to a promoter such that the anti-sense strand of RNA will be transcribed. The construct is then transformed into plants and the antisense strand of RNA is produced. In plant cells, it has been shown that antisense RNA inhibits gene expression by preventing the accumulation of mRNA which encodes the enzyme of interest, see, e.g., Sheehy et al., *Proc. Nat'l. Acad. Sci* (*USA*) 85:8805–8809 (1988); and Hiatt et al., U.S. Pat. No. 4,801,340.

Another method of suppression is sense suppression. Introduction of nucleic acid configured in the sense orientation has been shown to be an effective means by which to block the transcription of target genes. For an example of the use of this method to modulate expression of endogenous genes see, Napoli et al., *The Plant Cell* 2:279–289 (1990) and U.S. Pat. No. 5,034,323.

Catalytic RNA molecules or ribozymes can also be used to inhibit expression of plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloff et al., Nature 334:585–591 (1988).

A variety of cross-linking agents, alkylating agents and radical generating species as pendant groups on polynucleotides of the present invention can be used to bind, label, detect, and/or cleave nucleic acids. For example, Vlassov, V. V., et al., *Nucleic Acids Res* (1986) 14:4065–4076, describe covalent bonding of a single-stranded DNA fragment with alkylating derivatives of nucleotides complementary to target sequences. A report of similar work by the same group is that by Knorre, D. G., et al., *Biochimie* (1985) 67:785–789. Iverson and Dervan also showed sequence-specific cleavage of single-stranded DNA meditated by incorporation of a modified nucleotide which was capable of activating cleavage (*J Am Chem Soc* (1987) 109:1241–1243). Meyer, R. B. et al., *J Am Chem Soc* (1989) 111:8517–8519, effect covalent crosslinking to a target nucleotide using an alkylating agent complementary to the single-stranded target nucleotide sequence. A photoactivated crosslinking to single-stranded oligonucleotides meditated by psoralen was disclosed by Lee, B. L., et al., *Biochemistry* (1988) 27:3197–3203. Use of crosslinking in triple-helix forming probes was also disclosed by Home et al., *J Am Chem Soc* (1990) 112:2435–2437. Use of N4, N4-ethanocytosine as an alkylating agent to crosslink to single-stranded oligonucleotides has also been described by Webb and Matteucci, *J Am Chem Soc* (1986) 108:2764–2765; *Nucleic Acids Res* (1986) 14:7661–7674; Feteritz et al., *J. Am. Chem. Soc.* 113:4000 (1991). Various compounds to bind, detect, label, and/or cleave nucleic acids are known in the art. See, for example, U.S. Pat. Nos. 5,543,507; 5,672,593; 5,484,908; 5,256,648; and 5,681,941.

Proteins

The isolated proteins of the present invention comprise a polypeptide having at least 10 amino acids encoded by any one of the polynucleotides of the present invention as discussed more fully, above, or polypeptides which are conservatively modified variants thereof. The proteins of the present invention or variants thereof can comprise any number of contiguous amino acid residues from a polypeptide of the present invention, wherein that number is selected from the group of integers consisting of from 10 to the number of residues in a full-length polypeptide of the present invention. Optionally, this subsequence of contiguous amino acids is at least 15, 16, 17, 18, 19, 20, 21, 22, 23, 24, 25, 26, 27, 28, 29, 30, 31, 32, 33, 34, 35, 37, 38, 39, or 40 amino acids in length, often at least 50, 55, 60, 65, 70, 75, 80, 85, 90, 95, or 100 amino acids in length.

As those of skill will appreciate, the present invention includes catalytically active polypeptides of the present invention (i.e., enzymes). Catalytically active polypeptides have a specific activity of at least 20%, 30%, or 40%, and preferably at least 50%, 60%, or 70%, and most preferably at least 80%, 90%, or 95% that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least 30%, 40%, or 50%, that of the native (non-synthetic), endogenous polypeptide; and more preferably at least 60%, 70%, 80%, or 90%. Methods of assaying and quantifying measures of enzymatic activity and substrate specificity ($k_{cat}/K_m$), are well known to those of skill in the art.

Generally, the proteins of the present invention will, when presented as an immunogen, elicit production of an antibody specifically reactive to a polypeptide of the present invention. Further, the proteins of the present invention will not bind to antisera raised against a polypeptide of the present invention, which has been fully immunosorbed with the same polypeptide. Immunoassays for determining binding are well known to those of skill in the art. A preferred immunoassay is a competitive immunoassay as discussed, infra. Thus, the proteins of the present invention can be employed as immunogens for constructing antibodies immunoreactive to a protein of the present invention for such exemplary utilities as immunoassays or protein purification techniques.

Expression of Proteins in Host Cells

Using the nucleic acids of the present invention, one may express a protein of the present invention in a recombinantly engineered cell such as bacteria, yeast, insect, mammalian, or preferably plant cells. The cells produce the protein in a non-natural condition. (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or regulatable), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter to direct transcription, a ribosome binding site for translational initiation, and a transcription/translation terminator. One of skill would recognize that modifications could be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located purification sequences. Restriction sites or termination codons can also be introduced.

A. Expression in Prokaryotes

Prokaryotic cells may be used as hosts for expression. Prokaryotes most frequently are represented by various strains of E. coli; however, other microbial strains may also be used. Commonly used prokaryotic control sequences which are defined herein include promoters for transcription initiation, optionally with an operator, along with ribosome binding sequences, include such commonly used promoters as the beta lactamase (penicillinase) and lactose (lac) promoter systems (Chang et al., Nature 198:1056 (1977)), the tryptophan (trp) promoter system (Goeddel et al., Nucleic Acids Res. 8:4057 (1980)) and the lambda derived P L promoter and N-gene ribosome binding site (Shimatake et al., Nature 292:128(1981)). The inclusion of selection markers in DNA vectors transfected in E coli. is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using Bacillus sp. and Salmonella (Palva et al., Gene 22: 229–235 (1983); Mosbach, et al., Nature 302:543–545 (1983)).

B. Expression in Eukaryotes

A variety of eukaryotic expression systems such as yeast, insect cell lines, plant and mammalian cells, are known to those of skill in the art. As explained briefly below, a polynucleotide of the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, F., et al., *Methods in Yeast Genetics*, Cold Spring Harbor Laboratory (1982) is a well recognized work describing the various methods available to produce the protein in yeast. Two widely utilized yeasts for production of eukaryotic proteins are *Saccharomyces cerevisiae* and *Pichia pastoris*. Vectors, strains, and protocols for expression in Saccharomyces and Pichia are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysine the cells and applying standard protein isolation techniques to the lists. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect, or plant origin. Illustrative cell cultures useful for the production of the peptides are mammalian cells. Mammalian cell systems often will be in the form of minelayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g. the CMV promoter, a HSV tk promoter or pgk (phosphoglycerate kinase) promoter), an enhancer (Queen et al., *Immunol. Rev.* 89:49 (1986)), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection.

Appropriate vectors for expressing proteins of the present invention in insect cells are usually derived from the SF9 baculovirus. Suitable insect cell lines include mosquito larvae, silkworm, armyworm, moth and Drosophila cell lines such as a Schneider cell line (See, Schneider, *J. Embryol. Exp. Morphol.* 27:353–365 (1987).

As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague, et al., *J. Virol.* 45:773–781 (1983)). Additionally, gene sequences to control replication in the host cell may be incorporated into the vector such as those found in bovine papilloma virus type-vectors. Saveria-Campo, M., Bovine Papilloma Virus DNA a Eukaryotic Cloning Vector in *DNA Cloning Vol. II a Practical Approach,* D. M. Glover, Ed., IRL Press, Arlington, Va. pp. 213–238(1985).

Transfection/Transformation of Cells

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method, which provides for effective transformation/transfection may be employed.

A. Plant Transformation

The genes of the present invention can be used to transform any plant. In this manner, genetically modified plants, plant cells, plant tissue, seed, and the like can be obtained. Transformation protocols may vary depending on the type of plant cell, i.e. monocot or dicot, targeted for transformation. Suitable methods of transforming plant cells include microinjection (Crossway et al., (1986) *BioTechniques* 4:320–334), electroporation (Riggs et al. (1986) *Proc. Natl. Acad. Sci. USA* 83:5602–5606, Agrobacterium mediated transformation (Hinchee et al., (1988) *Biotechnology* 6:915–921; U.S. Pat. No. 5,981,840 (maize); U.S. Pat. No. 5,932,782 (sunflower), European patent No. 0486233 (sunflower); PCT application number WO 98/49332 (sorghum)), direct gene transfer (Paszkowski et al., (1984) *EMBO J.* 3:2717–2722), and ballistic particle acceleration (see, for example, Sanford et al., U.S. Pat. No. 4,945,050; Tomes et al., "Direct DNA Transfer into Intact Plant Cells via Microprojectile Bombardment" In Gamborg and Phillips (Eds.) *Plant Cell, Tissue and Organ Culture: Fundamental Methods,* Springer-Verlag, Berlin (1995); McCabe et al., (1988) *Biotechnology* 6:923–926); U.S. Pat. No. 5,990,387 (maize), U.S. Pat. No. 5,886,244 (maize); U.S. Pat. No. 5,322,783 (sorghum)). Also see, Weissinger et al., (1988) *Annual Rev. Genet.* 22:421–477; Sanford et al., (1987) *Particulate Science and Technology* 5:27–37 (onion); Christou et al., (1988) *Plant Physiol.* 87:671–674 (soybean); McCabe et al., (1988) *Bio/Technology* 6:923–926 (soybean); Datta et al., (1990) *Biotechnology* 8:736–740 (rice); Klein et al., (1988) *Proc. Natl. Acad. Sci. USA* 85:4305–4309 (maize); Klein et al., (1988) *Biotechnology* 6:559–563 (maize); Tomes et al., "Direct DNA Transfer into Intact Plant Cells via Microprojectile Bombardment" in Gamborg and Phillips (Eds.) *Plant Cell, Tissue and Organ Culture: Fundamental Methods,* Springer-Verlag, Berlin (1995) (maize); Klein et al., (1988) *Plant Physiol.* 91:440–444 (maize) Fromm et al., (1990)*Biotechnology* 8:833–839 (maize); Hooydaas-Van Slogteren & Hooykaas (1984) *Nature (London)* 311:763–764; Bytebier et al., (1987) *Proc. Natl. Acad. Sci. USA* 84:5345–5349 (Liliaceae); De Wet et al., (1985) In *The Experimental Manipulation of Ovule Tissues* ed. G. P. Chapman et al., pp. 197–209. Longman, NY (pollen); Kaeppler et al., (1990) *Plant Cell Reports* 9:415–418; and Kaeppler et al., (1992) *Theor. Appl. Genet.* 84:560–566 (whisker-meditated transformation); D'Halluin et al., (1992) *Plant Cell* 4:1495–1505 (electroporation); LI et al., (1993) *Plant Cell Reports* 12:250–255 and Christou and Ford (1995) *Annals of Botany* 75:745–750 (maize via *Agrobacterium tumefaciens*); all of which are herein incorporated by reference.

The cells, which have been transformed, may be grown into plants in accordance with conventional ways. See, for example, McCormick et al. (1986) *Plant Cell Reports,* 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved. One of skill will recognize that after the recombinant expression cassette is stably incorporated in transgenic plants and confirmed to be operable, it can be introduced into other plants by sexual crossing. Any of number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Backcrossing to a parental plant and out-crossing with a non-transgenic plant are also contemplated.

B. Transfection of Prokaryotes, Lower Eukaryotes, and Animal Cells

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextrin, electroporation, biolistics, and micro-injection of the DNA directly into the cells. The transfected cells are cultured by means well known in the art. Kuchler, R. J., *Biochemical Methods in Cell Culture and Virology*, Dowden, Hutchinson and Ross, Inc (1997).

Modulating Polypeptide Levels and Increasing Resistance to a Pathogen

The present invention further provides a method for modulating (i.e., increasing or decreasing) the concentration or composition of the polypeptides of the present invention in a plant or part thereof. Increasing or decreasing the concentration and/or the composition (i.e., the ratio of the polypeptides of the present invention) in a plant can effect modulation. The method comprised introducing into a plant cell with a recombinant expression cassette comprising a polynucleotide of the present invention as described above to obtain a transformed plant cell, culturing the transformed plant cell under plant cell growing conditions, and inducing or repressing expression of a polynucleotide of the present invention in the plant for a time sufficient to modulate concentration and/or composition in the plant or plant part.

In some embodiments, the content and/or composition of polypeptides of the present invention in a plant may be modulated by altering, in vivo or in vitro, the promoter of a gene to up- or down- regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et al., PCT/US93/03868. And in some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate the concentration and/or composition of polypeptides of the present invention in the plant. Plant forming conditions are well known in the art and discussed briefly, supra.

In general, concentration or composition is increased or decreased by at least 5%, 10%, 20%, 30%, 40%, 50%, 60%, 70%, 80%, or 90% relative to a native control plant, plant part, or cell lacking the aforementioned recombinant expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds, which activate expression from these promoters, are well known in the art. In preferred embodiments, the polypeptides of the present invention are modulated in monocots, particularly maize.

Although not to be limited by theory, overexpression of the lipoxygenase of the present invention in transgenic crops, especially in maize, may induce production of antimicrobial compounds or agents in the signaling pathways that trigger host plant defense mechanisms thereby inferring resistance against a variety of pathogens. Overexpression could also lead to the production of higher levels of signaling molecules, or even novel signaling molecules via protein engineering, that could alter fungal metabolism, sporulation or mycotoxin production.

Increased resistance could be engineered by overexpression of lipoxygenases either constitutively or under pathogen-inducible or stress-inducible expression, resulting in elevated levels of signaling molecules leading to a resistance response (e.g. jasmonic acid or another product of oxylipin pathways), or from the increased levels of directly antifungal metabolites such as hexanals, resulting from the action of hydroperoxide lyases on the products of lipoxygenase activity. In addition, overexpression of lipoxygenases may be desired in specific plant tissues. Therefore, the use of a tissue-preferred promoter may be used.

Reducing Aflatoxin Contamination of Grain by Modulating the Expression of CSSAP92

As described in Example 4 below, the expression of CSSAP92 alters the levels of aflatoxin accumulation in maize. The CSSAP92 gene is differentially expressed in maize lines with different degrees of susceptibility to *Aspergillus flavus* infections. Upon infection by *A. flavus* mRNA accumulation is observed in infected embryos of susceptible lines, but is not expressed or is reduced in message accumulation during infection of resistant lines. Therefore by reducing the expression of CSSAP92 during pathogen infection aflatoxin accumulation can be reduced.

Reduction in the expression of CSSAP92 can be accomplished by a number of methods, including but not limited to, antisense, catalytic RNA molecules (ribozymes), cross-linking agents, alkylating agents, radical generating species, or sense suppression. A discussion of these methods can be found in the section entitled "Recombinant Expression Cassettes." If suppression of CSSAP92 is only desired during pathogen infection, then a pathogen inducible promoter operably linked to the CSSAP92 polynucleotide in the sense orientation for sense suppression or antisense orientation for antisense suppression may be used. Alternatively a constitutive promoter operably linked to CSSAP92 in the sense or antisense orientation may be used. The recombinant expression cassette can then be transformed into plant cells and a whole plant can be regenerated.

Alternatively, the native cssap92 gene can be modified by chimeric oligonucleotides. U.S. Pat. No. 5,565,350 describes chimeric oligonucleotides that are useful for targeted gene correction and methods for their use in cultured mammalian cells. The use of chimeric oligonucleotides in plants is described in PCT Publication No. WO 99/25853, published May 27, 1999. Both disclosures are herein incorporated by reference. Briefly, oligonucleotides can be designed to modify naturally occurring or native nucleotide sequences in plants by at least one nucleotide using the sequence information of the present invention. The chimeric oligonucleotides are designed as a single molecule, with two sequences that are inverted and complementary, capable of folding back on itself to form a duplex structure. The oligonucleotide comprises DNA residues with at least two intervening blocks of 2'-O-methyl RNA residues flanking a short stretch of DNA residues, a DNA block. The number of RNA residues may vary. Usually, from about three to about twenty, preferably about four to about fifteen residues are utilized, more preferably about five to about ten residues.

The region of DNA flanked by the RNA regions is designed to introduce alterations in the target or complementing nucleotide sequence in the plant cell. Thus, it is recognized that the region of DNA residues, which are flanked by the RNA residues may vary depending upon the changes to be incorporated into the native gene. That is, where a single point mutation is being inserted, a short stretch of DNA residues is utilized, generally from about three to about eight, preferably about five. Where multiple residues are being inserted into the plant genome, longer stretches of DNA will be necessary. Likewise, where more than one point mutation is being made, the stretch of DNA will be determined by the location of the specific site changes. Thus, it is recognized that the length of the DNA block or modifying sequence, may vary from about five to more than about 60 nucleotides; preferably from about eight to about 50 nucleotides, more preferably from about 10 to about 30 nucleotides.

In addition, the expression of CSSAP92 may be reduced by the use of hairpin dsRNA techniques. These techniques are illustrated in PCT published applicant No. WO 99/53050, published Oct. 21, 1999 and WO 98/53083 published Nov. 26, 1998, both of which are herein incorporated by reference.

Molecular Markers

The present invention provides a method of genotyping a plant comprising a polynucleotide of the present invention. Optionally, the plant is a monocot, such as maize or sorghum. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology. A Laboratory Manual*, Chapter 7, Clark, Ed., Springer-Verlag, Berlin (1997). For molecular marker methods, see generally, The DNA Revolution by Andrew H. Paterson 1996 (Chapter 2) in: Genome Mapping in Plants (ed. Andrew H. Paterson) by Academic Press/R.G. Lands Company, Austin, Texas, pp. 7–21.

The particular method of genotyping in the present invention may employ any number of molecular marker analytic techniques such as, but not limited to, restriction fragment length polymorphism's (RFLPs). RFLPs are the product of allelic differences between DNA restriction fragments resulting from nucleotide sequence variability. As is well known to those of skill in the art, RFLPs are typically detected by extraction of genomic DNA and digestion with a restriction enzyme. Generally, the resulting fragments are separated according to size and hybridized with a probe; single copy probes are preferred. Restriction fragments from homologous chromosomes are revealed. Differences in fragment size among alleles represent an RFLP. Thus, the present invention further provides a means to follow segregation of a gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2, or 1 cM of a gene of the present invention.

In the present invention, the nucleic acid probes employed for molecular marker mapping of plant nuclear genomes selectively hybridize, under selective hybridization conditions, to a gene encoding a polynucleotide of the present invention. In preferred embodiments, the probes are selected from polynucleotides of the present invention. Typically, these probes are cDNA probes or restriction enzyme treated (e.g., PSTI) genomic clones. The length of the probes is discussed in greater detail, supra, but is typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in haploid chromosome compliment. Some exemplary restriction enzymes employed in RFLP mapping are EcoRI, EcoRv, and SstI. As used herein the term "restriction enzyme" includes reference to a composition that recognizes and, alone or in conjunction with another composition, cleaves at a specific nucleotide sequence.

The method of detecting an RFLP comprises the steps of (a) digesting genomic DNA of a plant with a restriction enzyme; (b) hybridizing a nucleic acid probe, under selective hybridization conditions, to a sequence of a polynucleotide of the present of said genomic DNA; (c) detecting therefrom a RFLP. Other methods of differentiating polymorphic (allelic) variants of polynucleotides of the present invention can be had by utilizing molecular marker techniques well known to those of skill in the art including such techniques as: 1) single stranded conformation analysis (SSCA); 2) denaturing gradient gel electrophoresis (DGGE); 3) RNase protection assays; 4) allele-specific oligonucleotides (ASOs); 5) the use of proteins which recognize nucleotide mismatches, such as the *E. coli* mutS protein; and 6) allele-specific PCR. Other approaches based on the detection of mismatches between the two complementary DNA strands include clamped denaturing gel electrophoresis (CDGE); heteroduplex analysis (HA); and chemical mismatch cleavage (CMC). Thus, the present invention further provides a method of genotyping comprising the steps of contacting, under stringent hybridization conditions, a sample suspected of comprising a polynucleotide of the present invention with a nucleic acid probe. Generally, the sample is a plant sample, preferably, a sample suspected of comprising a maize polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a polynucleotide of the present invention.

The product specificity analysis of the CSSAP92 protein shows it preferentially adds oxygen to the $9^{th}$ carbon of linoleic acid. The resulting product of 9 hydroxy linoleic acid has been implicated as an aflatoxin signaling molecule. Therefore, the CSSAP92 polynucleotide could also be used as a biomarker indicative of aflatoxin resistance in maize lines. There are several possible methods, well known in the art, for using polynucleotides as biomarkers. For example, antibodies to the CSSAP92 polynucleotide could be generated and then used to screen maize lines for those lines expressing the lowest level of the enzyme in the seed. The lower expressing CSSAP92 allele could then be cloned and used to identify allele-specific variations in the form of single nucleotide polymorphisms (SNP) or single sequence repeats (SSR). The SNP's or SSR's can then be used as a marker for the low-abundance allele of CSSAP92. Alternatively, a direct ELISA using the antibody to CSSAP92 could be used. The resulting SNP or SSR would then be used to track this allele in crosses or in a germplasm collection. The best region to identify SNP's that are allele-specific to the CSSAP92 polynucleotide is the 3' UTR of CSSAP92, found in SEQ ID NO: 5.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, *Nucleic Acids Res* 15:8125 (1987)) and the 7-methylguanosine cap structure (Drummond et al., *Nucleic Acids Res.* 13:7375 (1985)). Negative elements include stable intramolecular 5' UTR stem-loop structures (Muesing et al., *Cell* 48:691 (1987)) and AUG sequences or short open reading frames preceded by an appropriate AUG in the 5' UTR (Kozak, supra, Rao et al., *Mol and Cell. Biol.* 8:284 (1988)). Accordingly, the present invention provides 5' and/or 3' UTR regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host such as to optimize the codon usage in a heterologous sequence for expression in maize. Codon usage in the coding regions of the polynucleotides of the present invention can be analyzed statistically using commercially available software packages such as "Codon Preference" available form the University of Wisconsin Genetics Computer Group (see Devereaux et al., *Nucleic Acids Res.* 12:387–395 (1984)) or MacVector 4.1 (Eastman Kodak Co., New Haven, Conn.). Thus, the present invention provides a codon usage frequency characteristic of the coding region of at least one of the polynucleotides of the present invention. The number of polynucleotides that can be used to determine a codon usage frequency can be any integer from 1 to the number of polynucleotides of the present invention as provided herein. Optionally, the polynucleotides will be full-length sequences. An exemplary number of sequences for statistical analysis can be at least 1, 5, 10, 20, 50, or 100.

Sequence Shuffling

The present invention provides methods for sequence shuffling using polynucleotides of the present invention, and compositions resulting therefrom. Sequence shuffling is described in PCT Publication No. WO 96/19256. See also, Zhang, J.-H., et al. *Proc. Natl. Acad. Sci. USA* 94:4504–4509 (1997). Generally, sequence shuffling provides a means for generating libraries of polynucleotides having a desired characteristic, which can be selected or screened for. Libraries of recombinant polynucleotides are generated from a population of related sequence polynucleotides, which comprise sequence regions, which have substantial identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be a decreased $K_m$ and/or increased $K_{cat}$ over the wild-type protein as provided herein. In other embodiments, a protein or polynucleotide generated from sequence shuffling will have a ligand binding affinity greater than the non-shuffled wild-type polynucleotide. The increase in such properties can be at least 110%, 120%, 130%, 140%, or at least 150% of the wild-type value.

Generic and Consensus Sequences

Polynucleotides and polypeptides of the present invention further include those having: (a) a generic sequence of at least two homologous polynucleotides or polypeptides, respectively, of the present invention; and, (b) a consensus sequence of at least three homologous polynucleotides or polypeptides, respectively, of the present invention. The generic sequence of the present invention comprises each species of polypeptide or polynucleotide embraced by the generic polypeptide or polynucleotide, sequence, respectively. The individual species encompassed by a polynucleotide having an amino acid or nucleic acid consensus sequence can be used to generate antibodies or produce nucleic acid probes or primers to screen for homologs in other species, genera, families, orders, classes, phylums, or kingdoms. For example, a polynucleotide having a consensus sequence from a gene family of *Zea mays* can be used to generate antibody or nucleic acid probes or primers to other Gramineae species such as wheat, rice, or sorghum. Alternatively, a polynucleotide having a consensus sequence generated from orthologous genes can be used to identify or isolate orthologs of other taxa. Typically, a polynucleotide having a consensus sequence will be at least 9, 10, 15, 20, 25, 30, or 40 amino acids in length, or 20, 30, 40, 50, 100, or 150 nucleotides in length. As those of skill in the art are aware, a conservative amino acid substitution can be used for amino acids, which differ amongst aligned sequence but are from the same conservative amino acid substitution group as discussed above. Optionally, no more than 1 or 2 conservative amino acids are substituted for each 10 amino acid length of consensus sequence.

Similar sequences used for generation of a consensus or generic sequence include any number and combination of allelic variants of the same gene, orthologous, or paralogous sequences as provided herein. Optionally, similar sequences used in generating a consensus or generic sequence are identified using the BLAST algorithm's smallest sum probability (P(N)). Various suppliers of sequence-analysis software are listed in chapter 7 of *Current Protocols in Molecular Biology*, F. M. Ausubel et al., Eds. Current Protocols, a joint venture between Greene Publishing Associates, Inc. and John Wiley & Sons, Inc. (Supplement 30). A polynucleotide sequence is considered similar to a reference sequence if the smallest sum probability in a comparison of the test nucleic acid to the reference nucleic acid is less than about 0.1, more preferably less than about 0.01, or 0.001, and most preferably less than about 0.0001, or 0.00001. Similar polynucleotides can be aligned and a consensus or generic sequence generated using multiple. sequence alignment software available from a number of commercial suppliers such as the Genetics Computer Group's (Madison, Wis.) PILEUP software, Vector NTI's (North Bethesda, Md.) ALIGNX, or Genecode's (Ann Arbor, Mich.) SEQUENCER. Conveniently, default parameters of such software can be used to generate consensus or generic sequences.

Although the present invention has been described in some detail by way of illustration and example for purposes of clarity of understanding, it will be obvious that certain changes and modifications may be practices within the scope of the appended claims.

EXAMPLE 1

This example describes the construction of the cDNA libraries.

Total RNA was isolated from maize B73 tissues with TRIzol Reagent (Life Technology Inc. Gaithersburg, Md.) using a modification of the guanidine isothiocyanate/acid-phenol procedure described by Chomczynski and Sacchi (Chomczynski, P., and Sacchi, *N. Anal. Biochem.* 162, 156 (1987)). The maize tissue was isolated at the intersection of the stalk and shank, including some internodal stalk and shank tissue of a maize plant. The maize plants were grown in the field, allowed to pollinate naturally and the tissue harvested 2–3 weeks after pollen shed. In brief, plant tissue samples were pulverized in liquid nitrogen before the addition of the TRIzol Reagent, and then were further homogenized with a mortar and pestle. Addition of chloroform followed by centrifugation was conducted for separation of an aqueous phase and an organic phase. The total RNA was recovered by precipitation with isopropyl alcohol from the aqueous phase.

The selection of poly(A)+RNA from total RNA was performed using PolyATact system (Promega Corporation, Madison WI). In brief, biotinylated oligo(dT) primers were used to hybridize to the 3' poly(A) tails on mRNA. The hybrids were captured using streptavidin coupled to paramagnetic particles and a magnetic separation stand. The mRNA was washed at high stringent condition and eluted by RNase-free deionized water.

cDNA synthesis was performed and unidirectional cDNA libraries were constructed using the SuperScript Plasmid System (Life Technology Inc. Gaithersburg, Md.). The first strand of cDNA was synthesized by priming an oligo(dT) primer containing a Not I site. The reaction was catalyzed by SuperScript reverse Transcriptase II at 45° C. The second strand of cDNA was labeled with alpha-$^{32}$P-dCTP and a portion of the reaction was analyzed by agarose gel electrophoresis to determine cDNA sizes. cDNA molecules smaller than 500 base pairs and unligated adaptors were removed by Sephacryl-S400 chromatography. The selected cDNA molecules were ligated into a pSPORT1 vector between the NotI and SalI sites.

EXAMPLE 2

This example describes cDNA sequencing and library subtraction.

Individual colonies were picked and DNA was prepared either by PCR with M13 forward primers and M13 reverse primers, or by plasmid isolation. All the cDNA clones were sequenced using M13 reverse primers.

cDNA libraries subjected to the subtraction procedure were plated out on 22×22 cm$^2$ agar plate at density of about 3,000 colonies per plate. The plates were incubated in a 37° C. incubator for 12–24 hours. Colonies were picked into 384-well plates by a robot colony picker, Q-bot (GENETIX Limited). These plates were incubated overnight at 37° C.

Once sufficient colonies were picked, they were pinned onto 22×22 cm$^2$ nylon membranes using Q-bot. Each membrane contained 9,216 colonies or 36,864 colonies. These membranes were placed onto agar plate with appropriate antibiotic. The plates were incubated at 37° C. for overnight.

After colonies were recovered on the second day, these filters were placed on filter paper prewetted with denaturing solution for four minutes, then were incubated on top of a boiling water bath for additional four minutes. The filters were then placed on filter paper prewetted with neutralizing solution for four minutes. After excess solution was removed by placing the filters on dry filter papers for one minute, the colony site of the filters were placed into Proteinase K solution, incubated at 37° C. for 40–50 minutes. The filters were placed on dry filter papers to dry overnight. DNA was then cross-linked to nylon membrane by UV light treatment.

Colony hybridization was conducted as described by Sambrook, J., Fritsch, E. F. and Maniatis, T., (in Molecular Cloning: A laboratory Manual, 2$^{nd}$ Edition). The following probes were used in colony hybridization:

1. First strand cDNA from the same tissue as the library was made from to remove the most redundant clones.
2. 48–192 most redundant cDNA clones from the same library based on previous sequencing data.
3. 192 most redundant cDNA clones in the entire corn sequence database.
4. A Sal-A20 oligo nucleotide TCG ACC CAC GCG TCC GAA AAA AAA AAA AAA AAA AAA, (SEQ ID NO: 4) removes clones containing a poly A tail but no cDNA.
5. cDNA clones derived from rRNA.

The image of the autoradiography was scanned into computer and the signal intensity and cold colony addresses of each colony was analyzed, re-arraying of cold-colonies from 384 well plates to 96 well plates was conducted using Q-bot.

EXAMPLE 3

This example describes identification of the gene from a computer homology search.

Gene identities can be determined by conducting BLAST (Basic Local Alignment Search Tool; Altschul, S. F., et al., (1993) J. Mol. Biol. 215:403–410; see also www.ncbi.nlm.nih.gov/BLAST/) searches under default parameters for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences are analyzed for similarity to all publicly available DNA sequences contained in the "nr" database using the BLASTN algorithm. The DNA sequences are translated in all reading frames and compared for similarity to all publicly available protein sequences contained in the "nr" database using the BLASTX algorithm (Gish, W. and States, D. J. Nature Genetics 3:266–272 (1993)) provided by the NCBI. In some cases, the sequencing data from two or more clones containing overlapping segments of DNA are used to construct contiguous DNA sequences.

Using the procedure above a full-length clone was found containing the CSSAP92 polynucleotide as shown in SEQ ID NO: 1 (coding sequence plus 3' and 5' untranslated regions) and SEQ ID NO: 2 (coding region only). A partial maize lipoxygenase gene has been described in Jensen, et al., Plant Molec Biol 33:605–614 (1997). This L2 lipoxygenase shares high homology to the maize lipoxygenase of the present invention but lacks 177 amino acids or 531 nucleotides of the N-terminus. Additional sequence analysis and comparison of SEQ ID NO: 1 to the L2 lipoxygenase and other monocot lipoxygenases indicate that a number of atypical frameshifts occurred in the L2 lipoxygenase due to possible sequencing error or some other genetic variation. The truncation directly impacts the derived protein sequence and therefore enzyme functionality.

EXAMPLE 4

The Effect of CSSAP92 Expression on Aflatoxin (AF) Accumulation

Plant Materials and Treatments

The maize cultivars used in this study were Asgrow 404 and Tx714, lines that are highly susceptible to AF in the field, and Tx772/Fr2128, Tex6, MASqK, and Tx772, lines that have shown some resistance to AF contamination in the field. Asgrow 404 is a commercial hybrid. Tx772, Tx714 and Tex6 are inbred lines. Tx772/Fr2128 is a hybrid of the two inbred lines Tx 772 and Fr2128. MASqK is a derived line from the MASqK population developed in Georgia. Prior to treatment, kernels were sterilized by immersion in 10% chlorox for three minutes followed by immersion in sterile water for three minutes. Seeds were inoculated with either *Aspergillus flavus* strain 12-S or a *Fusarium verticillioides* isolate. To sterilize, kernels were immersed for 30 minutes in 0.1% tween 80 containing $10^6$ spores/ml. Control kernels were immersed in tween water for 30 minutes. Neither tween 80 or tween 20 effected lipoxygenase gene expression. Corn kernels were wounded using a sterile needle to pierce by the center of the embryo to a depth of approximately 1 mm. To determine the effects of methyl jasmonate on LOX gene expression, corn kernels were treated with a racemic mixture as previously described for peanut seed (Burow et al., Plant Mol. Biol. 42:689–701 (2000)). All treated and control seed were incubated in the dark at 30° C. in petri dishes containing moist filter paper and a water reservoir. Samples were collected at the indicated time points.

For all RNA studies, only the maize embryo was used. The embryo was removed by wrapping the seed in the folds of a paper towel and striking carefully with a hammer to crack the kernel. The endosperm, aleurone layer and scutellum were discarded and the embryo frozen in liquid nitrogen. Embryos were stored at −80° C.

RNA and DNA Extraction

RNA was isolated from kernel embryos, leaf, root and stem using Trizol reagent (GIBCO-BRL) following the manufacturer's protocol with modifications. Two embryos (approximately 150 mg) were used per extraction, or 150 mg of leaf, root and stem, which were lyophilized overnight and ground in liquid nitrogen. One ml of Trizol was added and the resulting aqueous phase extracted with phenol:chloroform and chloroform:isoamyl alcohol, and the RNA precipitated with isopropyl alcohol. The RNA was resuspended in water, and then reprecipitated in 8M LiCl followed by a second reprecipitation in 3M NaOAc and resuspension in 22 µl water. All solutions used were prepared with DEPC-treated water.

Genomic DNA was isolated from young leaf tissue following the urea extraction procedure of Chen and Dellaporta, The Maize handbook, Springer-Verlag, New York, Inc. (1993). Two grams of leaf was used per six ml of lysis buffer.

Northern Blot Analysis

Five µg of RNA were separated on a 1.2% agarose- 1.5% formaldehyde gel. RNA was transferred to Hybond membrane (Amersham). Following prehybridization and addition of the probe, the membranes were hybridized overnight at 60° C., and washed with increasing stringency up to 0.1× SSC, 0.1% SDS at 60° C.

Probes were obtained from the EST-clones by releasing the LOX inserts from the pSPORT1 cDNA cloning vector using the directional cloning restriction sites SalI (at the 5' end) and NotI (at the 3' end). The inserts were labeled with $^{32}$p using the random primer method (Sambrook et al., Molecular Cloning: A Laboratory Manual, 2d, Cold Spring Harbour Press, Cold Spring Harbour, N.Y. (1989)). For analysis of cssap 92 expression, digestion of the cssap 92 cDNA clone with SalI and NotI yielded two fragments; a 234 base pair SalI fragment from the 5' end of the gene and an approximately 2.6 Kb SalI-NotI fragment. Both fragments were purified, radiolabeled and used as probes in the RNA analysis. To confirm the 2.6 Kb SalI-NotI fragment was only hybridizing to the cssap 92 transcript, RNA blots were stripped and probed with an approximately 0.2 kb KpnI-NotI fragment containing the more variable 3' UTR end of the cssap 92 gene.

Southern Blot Analysis

Two µg of maize genomic DNA were digested with EcoRI, HindIII or XbaI, and separated on a 0.8% agarose gel by electrophoresis. The DNA was transferred to Hybond membranes after denaturation in 0.4 M NaOH solution. Membranes were probed with the 0.2 Kb KpnI-NotI fragment containing the 3' UTR of the cssap 92 gene in conditions described above for RNA blots.

Expression of the cssap 92 LOX Gene in *E. coli*

The full length cssap 92 cDNA clone was ligated into the expression vector pET30a (Novagen). This was achieved by isolating a 2.6 Kb SalI-NotI fragment of cssap 92, removing the SalI-NotI fragment from the pET30a vector, and subcloning the cssap 92 fragment directly into pET30 a to give pRAW1. pRAW1 encodes for 2.6 kb of the cssap 92 and lacks approximately 0.24 kb of the 5' coding region, including the putative start site. Next, approximately 0.3 kb of the 5' end of cssap 92 was amplified from the pSPORT1 vector using pfu polymerase (Stratagene) to introduce a unique NcoI site at the ATG codon. The PCR product and pRAW1 were digested with NcoI and SalI, and the PCR product was ligated into pRAW1 to give pRAW2. Plasmid pRAW2 encodes the full-length cssap 92 coding region in frame with the pET30a start site and preceded by the oligomeric histidine purification tag. The pRAW1 and pRAW2 were maintained in DH5 *E. coli cells and transformed into the BL*21 (DE3) strain of *E. coli* for induction of the CSSAP 92 protein. Induction was carried out following previously described protocols (Steczko et al, *Prot. Express. Pur.* 2:221–227 (1991)). Best results were obtained when cells were incubated at 15° C. for 20 hours, 300 rpm shaking, with 1 mM IPTG.

Analysis of the Oxidation Products of pRAW2 and pRAW1

Total protein was extracted from bacteria containing pRAW1, pRAW2 and the pET30a vector as described previously (Steczko et al., supra). LOX activity of the extracts was assayed spectrophotometrically. Extracts were stored in dry ice prior to incubation with linoleic acid. Protein extracts were thawed and an aliquot diluted in 24 ml of 50 mM HEPES, pH 7.0 and 50 µl of 48 mM methanolic linoleic acid at 25° C. (final pH of 6.9). The solution was magnetically stirred in a 125 ml Erlenmeyer flask for 15 minutes, after which time the pH of the reaction was adjusted to pH 4.0 with 1 M oxalic acid. 75 ml of CHCl$_3$/methanol (2:1, v/v) was immediately added to extract the products. The hydroperoxide derivatives contained in the bottom CHCl$_3$ layer were analyzed for positional and stereochemical properties as described previously (Gardner et al., *J. Am. Oil Chem. Soc.*, 75:1801–1808 (1998)).

Analysis of the Oxidation Products of Endogenous Maize LOXs

Maize seeds from Asgrow 404 and Tx772/Fr2128 lines inoculated with *A. flavus* or mock inoculated were ground in a coffee grinder. Four maize seeds per time point were combined in each case. Fifty mM HEPES (pH 7.0) was added at a rate of 10 ml/g maize meal and the slurry homogenized for one minute at full speed. After centrifugation at 10,000 g for 20 minutes, the fat layer was aspirated and a 0.25 ml aliquot of supernatant was stored at −20° C. for protein concentration determination. The remainder of the supernatant was added to a 125 ml Erlenmeyer flask followed by addition of HEPES buffer (pH 7.0) to give a maize extract:HEPES buffer ratio of 1:1.5 (v/v). The solution was stirred magnetically at a constant temperature of 25° C. The substrate solution contained 140 mg linoleic acid in 5 ml methanol, and was added by injection to the maize/HEPES buffer mix at a rate of 5 µl methanolic linoleic acid solution per 5 ml maize/HEPES mix to give a final concentration of 0.1 mM linoleic acid. After 15 minutes incubation at 25° C. with stirring, the reaction was stopped by adjusting the pH to 4.0 with oxalic acid and extracting the products with a volume of CHCl$_3$/methanol (2:1 v/v) equivalent to three times the volume of the reaction mix. The CHCl$_3$ extract could be saved at −20° C. until product analysis. Products were analyzed by gas chromatography-mass spectrometry as described in Burow et al., *Plant Mol. Biol.* 42:689–701 (2000), and the α-ketol products were examined as methyl ester/trimethylsilyoxy derivatives after NaBH$_4$ reduction giving two separable diastereoisomers for each α-ketol, e.g., two seperable methyl di-9, 10-trimethylsilyloxy-12(Z)-octadecenoates.

Aflatoxin B1 Quantitation

Maize seeds from Asgrow 404 and Tx772/Fr2128 lines inoculated with *A. flavus*, were ground under liquid nitrogen using a mortar and pestle and transferred to a 1.5 ml eppendorf. The sample was weighed and 500 µl of 70% MeOH added. The sample was vortexed vigorously, spun briefly in a centrifuge, and left to sit overnight at room temperature in the dark. Following a brief vortex and centrifugation, an aliquot of the MeOH layer was diluted 1 to 5 with 0.01 M PBS, and 50 µl of the diluted samples were used for ELISA measurements. Aflatoxin B1 concentration was determined by indirect competitive ELISA using standards of known AFB1 concentrations. Treatments were performed in triplicate and analyzed by the SAS statistical package.

The LOX Clone cssap 92

The cssap 92 clone was radiolabeled and used to probe total RNA, extracted over a 48 hour time course, from Tx772/Fr2128 maize embryos that had been (i) inoculated with *A. flavus*, (ii) not inoculated but allowed to germinate, and (iii) mock inoculated (control). The cssap 92 gene was expressed in germinating tissues and in the control, but was absent, or present at reduced levels, in embryos infected with *A. flavus*. Identical results were achieved using the 3' end of cssap 92 as a gene specific probe for this transcript.

To ensure cssap 92 was a unique *A. flavus* responsive LOX genes, the 3' end of cssap 92 was radiolabeled and used to probe digested genomic DNA. In the Southern hybridization analyses, the cssap 92 probe hybridized to only one band, suggesting it was specific to cssap 92.

Sequence analysis of the 5' and 3' ends of the cssap 92 EST clone indicated that the EST-clone probably contained the full-length transcript of cssap 92. Sequencing of the internal portion of cssap 92 showed that it appeared to encode for an allele of the previously published partial cDNA clone, L2, of maize. Over the region of overlap, cssap 92 shares 94% identity with L2 at the nucleotide and amino acid level. The cssap 92 clone is a full-length transcript, and relative to the partial L2 clone has an extra 177 codons, including a putative ATG start site determined by sequence homology with barley LOX1 and confirmed by obtaining active protein translated from this codon.

The cssap 92 Polynucleotide is Differentially Expressed in Embryos of Maize Cultivars Infected with *Aspergillus flavus*

There is a delay in the induction of expression of cssap 92 in *A. flavus* infected embryos of Tx772/Fr2128 compared to control embryos. To investigate whether this dampening of LOX expression (in comparison to control) was a conserved feature of maize kernel response to Aspergillus infections, cssap 92 expression was examined in several lines of maize varying in degrees of susceptibility to Aspergillus colonization and AF contamination. The expression of cssap 92 in control and *A. flavus* infected embryos of Asgrow 404, a commercial seed line susceptible to AF contamination was compared. RNA was isolated from control and *A. flavus* infected embryos of Asgrow 404 at 4, 8, 12, 24, 48, and 72 hour time points. RNA was probed with cssap 92.

In the Asgrow 404 line, there are similar levels of cssap 92 expression in both the control and infected embryos up to 48 hours post-inoculation. However, at 48 hours and beyond, cssap 92 expression increases dramatically in the infected embryos compared to the control. This is in contrast to the decreased cssap 92 expression in the infected embryos of Tx772/Fr2128 at 48 hours.

The 0.26 kb 3' end of the cssap 92 gene was used to probe total RNA of embryos from the corn lines MASqK (resistant), Tex 6 (resistant), Tx772 (resistant) and Tx714 (susceptible). RNA was extracted from *A. flavus* and germinating embryos. The control embryos were non-infected, non-germinating embryos. All RNA was extracted at a single time point of 48 hours post-inoculation.

Northern blot analysis shows that the patterns of cssap 92 expression differ between the different maize lines. Although expression of cssap 92 in the control embryos does not show any consistent pattern between the resistant or susceptible lines, it is most interesting to note that in infected embryos a definite pattern can be seen. Accumulation of cssap 92 mRNA is observed in infected embryos of susceptible lines, but is not expressed or is reduced in message accumulation during infection of resistant lines at the time points examined.

Thus, transcript analysis indicates that cssap 92 is differentially expressed in maize lines showing different degrees of susceptibility to AF contamination. The corn lines Tx772/Fr2128, Tx722, Tex6 and MASqK showed low levels of expression of the cssap 92 transcript in infected embryos. These four lines show some resistance to AF in the field. Asgrow 404 and Tx714 are susceptible to AF contamination in the field and both have increased expression of the cssap 92 transcript in infected embryos. These results are similar to those observed for some expressed plant defense genes in compatible or incompatible interactions with other pathogens. The POTLX-3 transcript (Kolomiets et al., *Plant Physiol.* 124:1121–1130 (2000)) accumulates steadily for several days during the resistance response of potato to *Phytophthora infestans*. However, in susceptible plants, POTLX-3 mRNA accumulation was delayed and inconsistent in the presence of *P. infestans*.

The cssap 92 Polynucleotide is Expressed in Root and Stem Tissue of Maize and is Induced by Wounding and Methyl Jasmonate To examine organ-specific expression in healthy plants, cssap 92 mRNA accumulation was also examined in leaf, root and stem tissues of Asgrow 404. The RNA was probed with the 0.26 kb 3' end of cssap 92. Expression of cssap 92 transcripts was not detected in young leaf, but like L2, was detected in root tissue. In addition, cssap 92 expression was observed in stem tissue.

Previously, using anti-serum capable of recognizing L2 and L1 lipoxygenase isoforms, Jensen et al, *Plant Mol. Biol.* 33:605–614 (1997) detected putative L2 protein in maize tissues after treatment with methyl jasmonate. Because Jensen et al., supra used a different corn line in their studies (W64A), and because of observed differential expression of cssap 92 in different lines in response to Aspergillus infection, the expression of cssap 92 was examined after treatment of embryos with methyl jasmonate and wounding in Asgrow 404 and Tx772/Fr2128. The results indicate that cssap 92 is expressed under all these conditions in both lines.

The cssap 92 Polynucleotide is Differentially Expressed in Maize Lines in Response to *Fusarium verticillioides*

Another serious mycotoxigenic fungus that frequently infects maize kernels is *Fusarium verticillioides* (formerly called *F. moniliforme*). To address the question of whether the expression of cssap 92 in response to *A. flavus* infection is a specific or general response to pathogen invasion, the expression of this gene was studied after inoculation with a strain of *Fusarium verticillioides* isolated from maize. Seeds of Asgrow 404 and Tx772/Fr2128 were challenged with *F. verticillioides*, *A. flavus*, and a water control. RNA was extracted from the embryos of these seeds at 24 and 48 hours post-inoculation. The Northern Blots were probed with the 0.26 kb 3' end of the cssap 92 gene. At 48 hours post-inoculation the levels of expression of cssap 92 in Asgrow 404 is higher for *A. flavus* infected seed than for *F. verticillioides* infected seed. The cssap 92 polynucleotide is more highly expressed in both *A. flavus* and *F. verticillioides* infected seed than it is in uninfected control seed. In Tx772/Fr2128, at 24 hours post-inoculation cssap 92 expression is only seen in the non-infected control seed. At 48 hours post-inoculation, similar levels of cssap 92 expression are seen in all three seed treatments.

Thus, in both lines, cssap 92 had the same pattern of expression in response to both fungi. Although not to be limited by theory, this suggests that the differential expression of cssap 92 seen in the different maize lines is a general mode of response to seed pathogens. However, in Asgrow 404, the level of gene expression was less during *F. verticillioides* infection than during *A. flavus* infection at the same time point.

In Vitro Expression of CSSAP 92 and Analysis of its Products

In order to determine the oxidation products of CSSAP 92, a full length cDNA was expressed in a bacterial expression system. The results can be seen in Table 1.

TABLE 1

| | 30 Percent of total | | | | | |
|---|---|---|---|---|---|---|
| | 13-HODEs | | | 9-HODEs | | |
| | 9(Z), 11(E)-diene | 9(E), 11(E)-diene | | 10(E), 12(Z)-diene | | 10(E), 12(E)-diene |
| Extract | 13(S) | 13(R) | 13(R,S) | 9(S) | 9(R) | 9(R,S) |
| pRaw2 (ph 7.0) | 0.27 | 0.65 | 0.63 | 95.7 | 0.4 | 2.4 |

TABLE 1-continued

| | 30 Percent of total | | | | | |
|---|---|---|---|---|---|---|
| | 13-HODEs | | | 9-HODEs | | |
| | 9(Z), 11(E)-diene | | 9(E), 11(E)-diene | 10(E), 12(Z)-diene | | 10(E), 12(E)-diene |
| Extract | 13(S) | 13(R) | 13(R,S) | 9(S) | 9(R) | 9(R,S) |
| pRaw1 (ph 12.5) | 50.7 | 12.1 | 8.7 | 11.6 | 10.3 | 6.6 |

Protein extracts from bacteria containing pRAW2 had measurable hydroperoxidizing activities over a pH range of 6.5 to 7.5. Maximum activity was observed at pH 7.0. No activity was seen from extracts of bacteria containing only the pET30a cloning vector or pRAW1 (encoding CSSAP 92 truncated at the N-terminus) at this pH. Activity at neutral pH suggested the major product of CSSAP 92 would be 9S-HPODE. In addition, the protein contains the bipartite TV motif, shown by Hornung et al., to specify 9S-HPODE production. (Hornung et al., Proc. Natl. Acad Sci. USA 96:4192–4197 (1999)) Examination of the hydroperoxy linoleic acid products confirms this is indeed the case as full-length CSSAP 92 protein produced 96% 9S-HPODE (Table 1). What little 13S-HPODE was present was largely racemic with some tendency toward (R) indicating some of the isomer arose from autoxidation or LOX-catalyzed autoxidation (Table 1). Because the (E,E)-diene isomers arise from rearrangements of peroxyl radicals, they are generally racemic and were not examined for (R,S)-stereoconfiguration. Interestingly, the CSSAP 92 protein lacking the N-terminus was weakly active at alkali pHs (12.5), suggesting it would produce mainly 13S-HPODE. Indeed 13S-HPODE is the major reaction product of the truncated protein at this pH (Table 1). The full length clone was not active at this pH.

Analysis of HPODE and AF Production in Two Maize Lines Inoculated with *A. flavus*

To couple expression data of cssap 92 (and other LOX genes) with activity and product specificity of the protein in situ, a series of control and infected seed (Asgrow 404 and Tx772/Fr2128) were examined for LOX activity at 0, 12, 24, 48 and 72 hr post-inoculation. The 9,10-ketol (analyzed as methyl 9,10-diOTMS derivative) was a major product in all cases. The 9,10-ketol arises from allene oxide synthase (AOS) action on 9S-HPODE (Gardner, Lipids 5:678–683 (1970)). Trace amounts of 12,13-ketols, derived from AOS action on 13S-HPODE, were detected in some samples. Therefore, the LOX proteins present in the mature seed are mainly 9S-HPODE producers.

Although 9S-HPODE is apparently present in seed under all conditions, the cssap 92 transcript, encoding a 9S-HPODE producer, nonetheless increases during infection in AF susceptible seed and is reduced in AF resistant seed. To see if this difference in cssap 92 expression is correlated with measurable differences in the concentration of AF produced by *A. flavus* growing on AF resistant or susceptible lines, the AF concentration was measured using the indirect competitive ELISA method for embryos extracted from the seed of Asgrow 404 and Tx772/Fr2128 contaminated with *A. flavus*. The amount of AF present in *A. flavus* infected Asgrow 404 and Tx772/Fr2128 seed at 0, 24, 48, 72 and 120 hours post-inoculation is shown in Table 2. Amounts are given in ppm. Aflatoxin was detected earlier in the Asgrow 404 seed (72 hours) but by 120 hours there was no significant difference in AF accumulation in the two lines.

TABLE 2

| Sample | Time post-inoculation (hrs) | AF concentration |
|---|---|---|
| Tx772/FR2128 | 12 | 0 |
| | 24 | 0 |
| | 48 | 0 |
| | 72 | 0 |
| | 120 | 32.8 +/− 8.8 |
| Asgrow 404 | 12 | 0 |
| | 24 | 0 |
| | 48 | 0 |
| | 72 | 10.4 +/− 3.1 |
| | 120 | 30.3 +/− 3.4 |

Although not to be limited by theory, it is possible that the differences in cssap 92 transcript levels (and possibly the amount of 9S-HPODE) in Asgrow 404 and Tx772/Fr2128 kernels could be a reflection of differences in mycotoxin production. Table 2 shows that seed of Asgrow 404 have measurable quantities of AF at earlier time points (72 hr) than seeds of Tx772/Fr2128. Because these lines are not isogenic, this difference could be due to differences in the way *A. flavus* grows and develops on the different maize seed. Whatever the reason, it is clear that Asgrow 404 is contaminated with more AF per gram of embryo at earlier time points than Tx772/Fr2128. This is consistent with the earlier appearance of the cssap 92 transcript in Asgrow 404. At 120 hours post-inoculation, the level of AF in both lines is very similar, suggesting cssap 92 expression in Tx772/Fr2128 is no longer delayed and contributes to AF production in the seed. The fact that Asgrow 404 expresses cssap 92 under infection conditions affords the potential for increased formation of 9S-HPODE and its major metabolite 9,10-ketol. Although 9S-HPODE increases AF gene expression, the effects of 9,10-ketol on AF production are not known. Nevertheless, these metabolites may explain increased AF gene expression in vitro. The differential expression of cssap 92 could explain why in both laboratory and field situations, Asgrow 404 exhibits more susceptibility to AF contamination than does Tx772/Fr2128.

To accurately determine the nature of the product specificity of CSSAP 92, the protein was purified and reacted with linoleic acid. The purified CSSAP 92 protein has a pH optimum of pH 7.0, indicative of a type 2 LOX. Intriguingly, an N-terminal truncated version of this protein, pRAW1, has very low but measurable activity at alkaline pH and produces mainly 13S-HPODE. From the structure of soybean lipoxygenase-1, it has been determined that the N-terminal region of the protein forms a beta-barrel structure (Boyington et al, Adv. Exp. Med Biol. 400A:133–138 (1997); Prigge et al., Biochimie 79:629–636 (1997)) shown to target lipid body lipoxygenase to liposomes and lipid bodies in cucumber seedlings (May et al., *Eur. J. Biochem.* 267:1100–1109 (2000)). With 13S-specific LOXs, H-removal and $O_2$ insertion occurs on opposite sides of the substrate to 9S-specific LOXs (Funk et al., *Biochemistry* 2621:6880–6884 (1987); Lehman, *J. Biol. Chem.* 242:5329–5335 (1994)). At high pH, the substrate molecule enters the active site in an orientation that favors 13S-HPODE production, presumably because the carboxylate anion prevents its insertion into the hydrophobic pocket of LOX in the inverse orientation. As the pH is lowered, the molecule reverses its orientation leading to more 9S-HPODE production (Gardner, *Biochem. Biophys. Acta.* 1084:221–239 (1989)). Although not to be limited by theory, deleting the N-terminal residues of CSSAP 92 could lead to a change in protein conformation and activity such that pRAW1 is only active at high pHs. At elevated pHs, the substrate molecule might only enter the active site in an orientation that leads to 13S-HPODE production.

Clearly, the cssap 92 polynucleotide, encoding a 9S-HPODE producing LOX, plays a contributing role in AF contamination. Expression of cssap 92 responds to *A. flavus* infestation. Moreover, its expression is also different in resistant and susceptible maize lines, with expression strongest during infection of susceptible lines. Because this work was performed under laboratory conditions, it most closely resembles the reaction of post-harvest seed to colonization during storage conditions.

The above examples are provided to illustrate the invention but not to limit its scope. Other variants of the invention will be readily apparent to one of ordinary skill in the art and are encompassed by the appended claims. All publications, patents, and patent applications cited herein are indicative of the level of those skilled in the art to which this invention pertains. All publications, patents, and patent applications are hereby incorporated by reference to the same extent as if each individual publication or patent application was specifically and individually indicated to be incorporated by reference.

What is claimed is:

1. An isolated nucleic acid comprising a polynucleotide selected from the group consisting of:
   (a) a polynucleotide that encodes a polypeptide of SEQ ID NO: 3;
   (b) a polynucleotide comprising the polynucleotide selected from the group consisting of SEQ ID NO: 1 and SEQ ID NO: 2; and
   (c) a polynucleotide complementary to a polynucleotide of (a) through (b).

2. A vector comprising at least one nucleic acid of claim 1.

3. A recombinant expression cassette, comprising the nucleic acid of claim 1 operably linked to a promoter, wherein the nucleic acid is in sense or antisense orientation.

4. A host cell comprising the recombinant expression cassette of claim 3.

5. A transgenic plant cell comprising the recombinant expression cassette of claim 3.

6. A transgenic plant comprising the recombinant expression cassette of claim 3.

7. The transgenic plant of claim 6, wherein the plant is maize, soybean, sunflower, sorghum, canola, wheat, alfalfa, cotton, rice, barley, and millet.

8. A transgenic seed from the transgenic plant of claim 7.

9. A method of modulating the level of lipoxygenase protein in a plant, comprising:
   (a) introducing into a plant cell with a recombinant expression cassette comprising a lipoxygenase polynucleotide that encodes the polypeptide of SEQ ID NO: 3 operably linked to a promoter;
   (b) culturing the plant cell under plant growing conditions to produce a regenerated plant; and
   (c) inducing expression of said polynucleotide for a time sufficient to modulate the level of lipoxygenase protein in said plant.

10. The method of claim 9, wherein the plant is maize, soybean, sunflower, sorghum, canola, wheat, alfalfa, cotton, rice, barley, and millet.

11. The method of claim 9, wherein the level of lipoxygenase protein is increased.

12. The method of claim 9, wherein the level of lipoxygenase protein is decreased.

13. The method of claim 9, wherein the polynucleotide comprises the polynucleotide selected from the group consisting of SEQ ID NO: 1 and SEQ ID NO: 2.

14. A method of decreasing accumulation of aflatoxin in a plant, comprising:
   (a) introducing into a plant cell a recombinant expression cassette comprising a lipoxygenase polynucleotide that encodes a polypeptide of SEQ ID NO: 3, operably linked to a promoter;
   (b) culturing the plant cell under plant growing conditions to produce a regenerated plant; and
   (c) inducing expression of said polynucleotide for a time sufficient to reduce aflatoxin accumulation in said plant.

15. The method of claim 14 wherein the plant cell is maize, soybean, sunflower, sorghum, canola, wheat, alfalfa, cotton, rice, barley, and millet.

16. The method of claim 14 wherein the polynucleotide comprises the polynucleotide selected from the group consisting of SEQ ID NO: 1 and SEQ ID NO: 2.

17. The method of claim 14 wherein the polynucleotide is in the antisense orientation.

18. The method of claim 14 wherein the polynucleotide is in the sense orientation.

19. A method of increasing resistance in a plant to a pathogen, comprising the steps of:
   a) introducing into a plant cell a recombinant expression cassette comprising the polynucleotide selected from the group consisting on SEQ ID NO: 1 and SEQ ID NO: 2 operably linked to a promoter;
   b) culturing the plant cell under plant growing conditions to produce a regenerated plant; and
   c) inducing expression of the polynucleotide for a time sufficient to increase the resistance to a pathogen in the plant.

20. The method of claim 19, wherein the plant cell is maize, soybean, sunflower, sorghum, canola, wheat, alfalfa, cotton, rice, barley, and millet.

21. The method of claim 19, wherein the promoter is a pathogen-inducible promoter.

22. The method of claim 19, wherein the promoter is a tissue-preferred promoter.

* * * * *

SEQUENCE LISTING

<160> NUMBER OF SEQ ID NOS: 5

<210> SEQ ID NO 1
<211> LENGTH: 3007
<212> TYPE: DNA
<213> ORGANISM: Zea mays

<400> SEQUENCE: 1

```
ccacgcgtcc gcacagacac caacgccact gcactgcaaa agcaagagca gctagctagt      60
aaagatgctg agcgggatca tcgacgggct gacggggggcg aacaagcatg cgcggctcaa    120
gggcacggtg gtgctcatgc gcaagaacgt gctggaccct aacgacttcg cgccaccgt     180 cgttgacagc atcagcgagt tcctcggcaa gggggtcacc tgccagctca tcagctccac    240
cctcgtcgac gccaacaacg gcaaccgcgg gcgggtcggg gcggaggcga acctggagca    300
gtggctgacg agcctgccgt cgctgacgac cggcgagtcc aagttcggcg tcacgttcga    360
ctgggaggtg gagaagctgg gagtgccggg ggccgtcgtc gtcaagaaca ccacgccgc     420 cgagttcttc ctcaagacaa tcaccctcga cgacgtgccc ggccgcggcg ccgtcacctt    480
cgtcgccaac tcctgggtct accccgcggg caagtaccgc tacaaccgcg tcttcttctc    540
caacgatacg tacctgccaa gccagatgcc ggcggcgctg aagccgtacc gcgacgacga    600
gctccgcaac ctccgcggcg acgaccagca gggcccctac caggagcacg accgcgtgta    660
ccgctacgac gtctacaacg acctcggcga gcccgacggc ggcaacccgc gcccatcct    720 cggcggctcc gccgaccacc cgtacccgcg ccgctgccgc acgggccgca agcccaccaa    780
aaccgacccc aactcggata gccgactgtc gctggtggag cagatctacg tgccgcggga    840
cgagcgcttc ggccacctca agatgtccga cttcctgggc tactccatca aggccatcac    900
gcagggcatc atcccggcgg tgcgcacgta cgtggacacc accccgggcg agttcgactc    960
cttccaggac atcatcaacc tgtacgaggg cgggatcaag ctgcccaaga tccaggcgct   1020
cgaggacatg cgcaagctct tcccgctcca gctcgtcaag gacctcctcc ccgccggcgg   1080
ggactacctg ctcaagctcc ccatcccaca gatcatccaa gaggacaaga acgcgtggag   1140
gaccgacgag gagttcgcgc gggaggtgct cgccggcgtc aacccgatgg tgatcacgcg   1200
cctcacggag ttcccgccca agagcacgct ggaccccagc aagtacggcg accacaccag   1260
```

```
cacgatcacg gcggagcaca tcgagaagaa cctcgagggc ctcacggtgc agcaggcgct   1320
ggacggcaac aggctctaca tcctggacca ccacgaccgc ttcatgccgt tcctcatcga   1380
cgtcaacaac ctggagggca acttcatcta cgccaccagg acgctcttct tcctgcgcgg   1440
cgacggcagg ctcgcgcccc tcgccatcga gctcagcgag ccgtacatcg acggggacct   1500
caccgtggcc aagagcaagg tctacacgcc ggcgtccagc ggcgtcgagg cctgggtgtg   1560
gcagctcgcc aaggcctatg tcgccgtcaa cgactctggc tggcaccaac tcgtcagcca   1620
ctggctgaac acccacgcgg tgatggagcc gttcgtgatc gcgacgaacc ggcagctgag   1680
cgtgacgcac ccggtgcaca agctcctgag ctcgcacttc cgcgacacca tgaccatcaa   1740
cgcgctggcc cggcagacgc tcatcaacgg cggcggcatc ttcgagatga ccgtcttccc   1800
gggcaagtac gcgctgggca tgtcctccgt ggtgtacaag agctggaact tcaccgagca   1860
gggcctcccc gccgacctcg tcaagagggg cgtggcggtg gcggacccgt ccagcccgta   1920
caaggtgcgg ctgctgatcg aggactaccc gtacgcgagc gacgggctgg ccatctggca   1980
cgccatcgag cagtgggtgg gcgagtacct ggccatctac taccccgacg acggcgcgct   2040
gcggggcgac gaggagctgc aggcgtggtg gaaggaggtg cgcgaggtcg gcacggcga   2100 ccacaaggac gcgccctggt ggcccaagat gcaggccgtg tcggagctcg ccagcgcctg   2160
caccaccatc atctggatcg cgtcggcgct ccacgccgcc gtcaacttcg ccagtaccc   2220 gtacgcgggg tacctcccga caggcccac ggtgagccgg cgccggatgc cggagcccgg   2280
cagcaaggag tacgaggagc tggagcgcga cccggagcgc ggcttcatcc acaccatcac   2340
gagccagatc cagaccatca tcggcatctc gctcatcgag atcctctcca gcactcctc   2400 cgacgaggtg tacctcggcc agcgcgacac ccccgagtgg acctccgacg cccgggcgct   2460
ggcggcgttc aagaggttca gcgacgcgct ggtcaagatc gagggcaagg tggtgggcga   2520
gaaccgcgac ccgcagctga ggaacaggaa cggccccgcc gagttcccct acatgctgct   2580
ctatcccaac acctctgacc acagtggcgc cgccgcaggg ctcactgcca agggcatccc   2640
caacagcatc tccatctgag cgactggtac cactaccacc ccaggagtgc tacgtacgag   2700
ctggtacatg aataagctaa tataagcaat cgtgtaaacg ggaagagagc ggccggcacg   2760
agacggacca tgtattttgc gtaaacgtgt gggctggtga atcgaattac taccacgtaa   2820
taagtgaagt gcttgttgca atcattggcc tgccagcttc aagattcttg cagttactat   2880
tctagtcgtt tcgcagtgct cctcgatcac aacatttcac gaggtgtttt attacaataa   2940
tttggagcta ttcaatttca aaaaaaaaa aaaaaaaaa aaaaaaaaa aaaaaaaaa   3000 aaaaaaa                                                              3007

<210> SEQ ID NO 2
<211> LENGTH: 2595
<212> TYPE: DNA
<213> ORGANISM: Zea mays

<400> SEQUENCE: 2
atgctgagcg ggatcatcga cgggctgacg ggggcgaaca agcatgcgcg gctcaagggc     60
acggtggtgc tcatgcgcaa gaacgtgctg gacctcaact acttcggcgc caccgtcgtt    120
gacagcatca gcgagttcct cggcaagggg gtcacctgcc agctcatcag ctccaccctc    180
gtcgacgcca acaacggcaa ccgcgggcgg gtcgggcgg aggcgaacct ggagcagtgg    240
ctgacgagcc tgccgtcgct gacgaccggc gagtccaagt tcggcgtcac gttcgactgg    300
```

-continued

```
gaggtggaga agctgggagt gccggggggcc gtcgtcgtca agaacaacca cgccgccgag      360
ttcttcctca agacaatcac cctcgacgac gtgcccggcc gcggcgccgt caccttcgtc      420
gccaactcct gggtctaccc cgcgggcaag taccgctaca accgcgtctt cttctccaac      480
gatacgtacc tgccaagcca gatgccggcg gcgctgaagc cgtaccgcga cgacgagctc      540
cgcaacctcc gcggcgacga ccagcagggc ccctaccagg agcacgaccg cgtgtaccgc      600
tacgacgtct acaacgacct cggcgagccc gacggcggca acccgcgccc catcctcggc      660
ggctccgccg accacccgta cccgcgccgc tgccgcacgg gccgcaagcc caccaaaacc      720
gaccccaact cggatagccg actgtcgctg gtggagcaga tctacgtgcc gcgggacgag      780
cgcttcggcc acctcaagat gtccgacttc ctgggctact ccatcaaggc catcacgcag      840
ggcatcatcc cggcggtgcg cacgtacgtg gacaccaccc cgggcgagtt cgactccttc      900
caggacatca tcaacctgta cgagggcggg atcaagctgc ccaagatcca ggcgctcgag      960
gacatgcgca agctcttccc gctccagctc gtcaaggacc tcctccccgc cggcggggac     1020
tacctgctca agctccccat cccacagatc atccaagagg acaagaacgc gtggaggacc     1080
gacgaggagt tcgcgcggga ggtgctcgcc ggcgtcaacc cgatggtgat cacgcgcctc     1140
acggagttcc cgcccaagag cacgctggac cccagcaagt acggcgacca caccagcacg     1200
atcacggcgg agcacatcga gaagaacctc gagggcctca cggtgcagca ggcgctggac     1260
ggcaacaggc tctacatcct ggaccaccac gaccgcttca tgccgttcct catcgacgtc     1320
aacaacctga agggcaactt catctacgcc accaggacgc tcttcttcct gcgcggcgac     1380
ggcaggctcg cgcccctcgc catcgagctc agcgagccgt acatcgacgg ggacctcacc     1440
gtggccaaga gcaaggtcta cacgccggcg tccagcggcg tcgaggcctg ggtgtggcag     1500
ctcgccaagg cctatgtcgc cgtcaacgac tctggctggc accaactcgt cagccactgg     1560
ctgaacaccc acgcggtgat ggagccgttc gtgatcgcga cgaaccggca gctgagcgtg     1620
acgcacccgg tgcacaagct cctgagctcg cacttccgcg acaccatgac catcaacgcg     1680
ctggcgcggc agacgctcat caacggcggc ggcatcttcg agatgaccgt cttcccgggc     1740
aagtacgcgc tgggcatgtc ctccgtggtg tacaagagct ggaacttcac cgagcagggc     1800
ctccccgccc acctcgtcaa gagggggcgtg gcggtggcgg acccgtccag cccgtacaag     1860
gtgcggctgc tgatcgagga ctacccgtac gcgagcgacg ggctggccat ctggcacgcc     1920
atcgagcagt gggtgggcga gtacctggcc atctactacc ccgacgacgg cgcgctgcgg     1980
ggcgacgagg agctgcaggc gtggtggaag gaggtgcgcg aggtcgggca cggcgaccac     2040
aaggacgcgc cctggtggcc caagatgcag gccgtgtcgg agctcgccag cgcctgcacc     2100
accatcatct ggatcgcgtc ggcgctccac gccgccgtca acttcggcca gtacccgtac     2160
gcggggtacc tcccgaacag gcccacggtg agccggcgcc ggatgccgga gcccggcagc     2220
aaggagtacg aggagctgga gcgcgacccg gagcgcggct tcatccacac catcacgagc     2280
cagatccaga ccatcatcgg catctcgctc atcgagatcc tctccaagca ctcctccgac     2340
gaggtgtacc tcggccagcg cgacaccccc gagtggacct ccgacgcccg ggcgctggcg     2400
gcgttcaaga ggttcagcga cgcgctggtc aagatcgagg gcaaggtggt gggcgagaac     2460
cgcgacccgc agctgaggaa caggaacggc cccgccgagt tcccctacat gctgctctat     2520
cccaacacct ctgaccacag tggcgccgcc gcagggctca ctgccaaggg catccccaac     2580
agcatctcca tctga                                                      2595
```

```
<210> SEQ ID NO 3
<211> LENGTH: 864
<212> TYPE: PRT
<213> ORGANISM: Zea mays

<400> SEQUENCE: 3
```

| | | | | | | | | | | | | | | | |
|---|---|---|---|---|---|---|---|---|---|---|---|---|---|---|---|
| Met | Leu | Ser | Gly | Ile | Ile | Asp | Gly | Leu | Thr | Gly | Ala | Asn | Lys | His | Ala |
| 1 | | | | 5 | | | | | 10 | | | | | 15 | |
| Arg | Leu | Lys | Gly | Thr | Val | Val | Leu | Met | Arg | Lys | Asn | Val | Leu | Asp | Leu |
| | | | 20 | | | | | 25 | | | | | 30 | | |
| Asn | Asp | Phe | Gly | Ala | Thr | Val | Val | Asp | Ser | Ile | Ser | Glu | Phe | Leu | Gly |
| | | 35 | | | | 40 | | | | | 45 | | | | |
| Lys | Gly | Val | Thr | Cys | Gln | Leu | Ile | Ser | Ser | Thr | Leu | Val | Asp | Ala | Asn |
| 50 | | | | | 55 | | | | | 60 | | | | | |
| Asn | Gly | Asn | Arg | Gly | Arg | Val | Gly | Ala | Glu | Ala | Asn | Leu | Glu | Gln | Trp |
| 65 | | | | | 70 | | | | | 75 | | | | | 80 |
| Leu | Thr | Ser | Leu | Pro | Ser | Leu | Thr | Thr | Gly | Ser | Lys | Phe | Gly | Val |
| | | | | 85 | | | | | 90 | | | | | 95 | |
| Thr | Phe | Asp | Trp | Glu | Val | Glu | Lys | Leu | Gly | Val | Pro | Gly | Ala | Val | Val |
| | | | 100 | | | | | 105 | | | | | 110 | | |
| Val | Lys | Asn | Asn | His | Ala | Ala | Glu | Phe | Phe | Leu | Lys | Thr | Ile | Thr | Leu |
| | | 115 | | | | 120 | | | | | 125 | | | | |
| Asp | Asp | Val | Pro | Gly | Arg | Gly | Ala | Val | Thr | Phe | Val | Ala | Asn | Ser | Trp |
| 130 | | | | | 135 | | | | | 140 | | | | | |
| Val | Tyr | Pro | Ala | Gly | Lys | Tyr | Arg | Tyr | Asn | Arg | Val | Phe | Phe | Ser | Asn |
| 145 | | | | | 150 | | | | | 155 | | | | | 160 |
| Asp | Thr | Tyr | Leu | Pro | Ser | Gln | Met | Pro | Ala | Ala | Leu | Lys | Pro | Tyr | Arg |
| | | | | 165 | | | | | 170 | | | | | 175 | |
| Asp | Asp | Glu | Leu | Arg | Asn | Leu | Arg | Gly | Asp | Asp | Gln | Gln | Gly | Pro | Tyr |
| | | | 180 | | | | | 185 | | | | | 190 | | |
| Gln | Glu | His | Asp | Arg | Val | Tyr | Arg | Tyr | Asp | Val | Tyr | Asn | Asp | Leu | Gly |
| | | 195 | | | | 200 | | | | | 205 | | | | |
| Glu | Pro | Asp | Gly | Gly | Asn | Pro | Arg | Pro | Ile | Leu | Gly | Gly | Ser | Ala | Asp |
| | 210 | | | | | 215 | | | | | 220 | | | | |
| His | Pro | Tyr | Pro | Arg | Arg | Cys | Arg | Thr | Gly | Arg | Lys | Pro | Thr | Lys | Thr |
| 225 | | | | | 230 | | | | | 235 | | | | | 240 |
| Asp | Pro | Asn | Ser | Asp | Ser | Arg | Leu | Ser | Leu | Val | Glu | Gln | Ile | Tyr | Val |
| | | | | 245 | | | | | 250 | | | | | 255 | |
| Pro | Arg | Asp | Glu | Arg | Phe | Gly | His | Leu | Lys | Met | Ser | Asp | Phe | Leu | Gly |
| | | | 260 | | | | | 265 | | | | | 270 | | |
| Tyr | Ser | Ile | Lys | Ala | Ile | Thr | Gln | Gly | Ile | Ile | Pro | Ala | Val | Arg | Thr |
| | | 275 | | | | 280 | | | | | 285 | | | | |
| Tyr | Val | Asp | Thr | Thr | Pro | Gly | Glu | Phe | Asp | Ser | Phe | Gln | Asp | Ile | Ile |
| | 290 | | | | | 295 | | | | | 300 | | | | |
| Asn | Leu | Tyr | Glu | Gly | Gly | Ile | Lys | Leu | Pro | Lys | Ile | Gln | Ala | Leu | Glu |
| 305 | | | | | 310 | | | | | 315 | | | | | 320 |
| Asp | Met | Arg | Lys | Leu | Phe | Pro | Leu | Gln | Leu | Val | Lys | Asp | Leu | Leu | Pro |
| | | | | 325 | | | | | 330 | | | | | 335 | |
| Ala | Gly | Gly | Asp | Tyr | Leu | Leu | Lys | Leu | Pro | Ile | Pro | Gln | Ile | Ile | Gln |
| | | | 340 | | | | | 345 | | | | | 350 | | |
| Glu | Asp | Lys | Asn | Ala | Trp | Arg | Thr | Asp | Glu | Glu | Phe | Ala | Arg | Glu | Val |
| | | 355 | | | | 360 | | | | | 365 | | | | |
| Leu | Ala | Gly | Val | Asn | Pro | Met | Val | Ile | Thr | Arg | Leu | Thr | Glu | Phe | Pro |
| | 370 | | | | | 375 | | | | | 380 | | | | |

-continued

```
Pro Lys Ser Thr Leu Asp Pro Ser Lys Tyr Gly Asp His Thr Ser Thr
385                 390                 395                 400

Ile Thr Ala Glu His Ile Glu Lys Asn Leu Glu Gly Leu Thr Val Gln
            405                 410                 415

Gln Ala Leu Asp Gly Asn Arg Leu Tyr Ile Leu Asp His His Asp Arg
                420                 425                 430

Phe Met Pro Phe Leu Ile Asp Val Asn Leu Glu Gly Asn Phe Ile
            435                 440                 445

Tyr Ala Thr Arg Thr Leu Phe Phe Leu Arg Gly Asp Gly Arg Leu Ala
450                 455                 460

Pro Leu Ala Ile Glu Leu Ser Glu Pro Tyr Ile Asp Gly Asp Leu Thr
465                 470                 475                 480

Val Ala Lys Ser Lys Val Tyr Thr Pro Ala Ser Ser Gly Val Glu Ala
                485                 490                 495

Trp Val Trp Gln Leu Ala Lys Ala Tyr Val Ala Val Asn Asp Ser Gly
            500                 505                 510

Trp His Gln Leu Val Ser His Trp Leu Asn Thr His Ala Val Met Glu
            515                 520                 525

Pro Phe Val Ile Ala Thr Asn Arg Gln Leu Ser Val Thr His Pro Val
            530                 535                 540

His Lys Leu Leu Ser Ser His Phe Arg Asp Thr Met Thr Ile Asn Ala
545                 550                 555                 560

Leu Ala Arg Gln Thr Leu Ile Asn Gly Gly Ile Phe Glu Met Thr
                565                 570                 575

Val Phe Pro Gly Lys Tyr Ala Leu Gly Met Ser Ser Val Val Tyr Lys
            580                 585                 590

Ser Trp Asn Phe Thr Glu Gln Gly Leu Pro Ala Asp Leu Val Lys Arg
            595                 600                 605

Gly Val Ala Val Ala Asp Pro Ser Ser Pro Tyr Lys Val Arg Leu Leu
            610                 615                 620

Ile Glu Asp Tyr Pro Tyr Ala Ser Asp Gly Leu Ala Ile Trp His Ala
625                 630                 635                 640

Ile Glu Gln Trp Val Gly Glu Tyr Leu Ala Ile Tyr Pro Asp Asp
                645                 650                 655

Gly Ala Leu Arg Gly Asp Glu Glu Leu Gln Ala Trp Trp Lys Glu Val
            660                 665                 670

Arg Glu Val Gly His Gly Asp His Lys Asp Ala Pro Trp Trp Pro Lys
            675                 680                 685

Met Gln Ala Val Ser Glu Leu Ala Ser Ala Cys Thr Thr Ile Ile Trp
690                 695                 700

Ile Ala Ser Ala Leu His Ala Ala Val Asn Phe Gly Gln Tyr Pro Tyr
705                 710                 715                 720

Ala Gly Tyr Leu Pro Asn Arg Pro Thr Val Ser Arg Arg Met Pro
                725                 730                 735

Glu Pro Gly Ser Lys Glu Tyr Glu Glu Leu Glu Arg Asp Pro Glu Arg
            740                 745                 750

Gly Phe Ile His Thr Ile Thr Ser Gln Ile Gln Thr Ile Gly Ile
                755                 760                 765

Ser Leu Ile Glu Ile Leu Ser Lys His Ser Ser Asp Glu Val Tyr Leu
            770                 775                 780

Gly Gln Arg Asp Thr Pro Glu Trp Thr Ser Asp Ala Arg Ala Leu Ala
785                 790                 795                 800

Ala Phe Lys Arg Phe Ser Asp Ala Leu Val Lys Ile Glu Gly Lys Val
```

-continued

```
                805                 810                 815
Val Gly Glu Asn Arg Asp Pro Gln Leu Arg Asn Arg Asn Gly Pro Ala
                820                 825                 830

Glu Phe Pro Tyr Met Leu Leu Tyr Pro Asn Thr Ser Asp His Ser Gly
        835                 840                 845

Ala Ala Ala Gly Leu Thr Ala Lys Gly Ile Pro Asn Ser Ile Ser Ile
    850                 855                 860

<210> SEQ ID NO 4
<211> LENGTH: 36
<212> TYPE: DNA
<213> ORGANISM: Artificial Sequence
<220> FEATURE:
<223> OTHER INFORMATION: Designed oligonucleotide based upon the adapter
      sequence and poly T to remove clones which have a poly A tail but
      no cDNA.

<400> SEQUENCE: 4
tcgacccacg cgtccgaaaa aaaaaaaaaa aaaaaa                              36

<210> SEQ ID NO 5
<211> LENGTH: 249
<212> TYPE: DNA
<213> ORGANISM: Zea mays

<400> SEQUENCE: 5
ctggtacatg aataagctaa tataagcaat cgtgtaaacg ggaagagagc ggccggcacg     60
agacggacca tgtattttgc gtaaacgtgt gggctggtga atcgaattac taccacgtaa   120
taagtgaagt gcttgttgca atcattggcc tgccagcttc aagattcttg cagttactat   180
tctagtcgtt tcgcagtgct cctcgatcac aacatttcac gaggtgtttt attacaataa   240
tttggagct                                                          249
```